US012692231B2

(12) United States Patent
Chadeayne

(10) Patent No.: US 12,692,231 B2
(45) Date of Patent: Jul. 28, 2026

(54) TRYPTAMINE DERIVATIVES

(71) Applicant: CAAMTECH, INC., Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

(21) Appl. No.: 18/855,893

(22) PCT Filed: Apr. 13, 2023

(86) PCT No.: PCT/US2023/065718

§ 371 (c)(1),
(2) Date: Oct. 10, 2024

(87) PCT Pub. No.: WO2023/201293

PCT Pub. Date: Oct. 19, 2023

(65) Prior Publication Data

US 2025/0129022 A1 Apr. 24, 2025

Related U.S. Application Data

(60) Provisional application No. 63/330,475, filed on Apr. 13, 2022, provisional application No. 63/330,469, (Continued)

(51) Int. Cl.

*C07D 209/16* (2006.01)
*A61K 31/4045* (2006.01)
*A61K 45/06* (2006.01)

(52) U.S. Cl.

CPC ........ *C07D 209/16* (2013.01); *A61K 31/4045* (2013.01); *A61K 45/06* (2013.01)

(58) Field of Classification Search

CPC .................................................... C07D 209/16
See application file for complete search history.

(56) References Cited

U.S. PATENT DOCUMENTS

2018/0221396 A1 8/2018 Chadeayne
2019/0142851 A1 5/2019 Chadeayne

FOREIGN PATENT DOCUMENTS

WO 2021/101926 A1 5/2021
WO 2021/188812 A1 9/2021

(Continued)

OTHER PUBLICATIONS

Morissette, High-throughput crystallization: polymorphs, salts, co-crystals, and solvates of pharmaceutical solids, Advanced Drug Delivery Reviews, 2004, 56, pp. 275-300 (Year: 2004).*

(Continued)

*Primary Examiner* — Renee Claytor
*Assistant Examiner* — Andrew P Lee
(74) *Attorney, Agent, or Firm* — RAPHAEL BELLUM PLLC

(57) ABSTRACT

The disclosure relates to (2-{4-[(methoxycarbonyl)oxy]-1H-indol-3-yl}ethyl)bis(propan-2-yl)azanium chloride (4-methylcarbonato-N,N-diisopropyltryptramine chloride or 4-methylcarbonato-DiPT chloride), crystalline 4-methylcarbonato-DiPT chloride, [2-(1H-indol-3-yl)ethyl](propan-2-yl)amine (N-isopropyltryptamine or NiPT), crystalline NiPT, N-[2-(1H-indol-3-yl)ethyl]propan-2-amine hydrobromide (N-isopropyltryptamine hydrobromide or NiPT hydrobromide), crystalline NiPT hydrobromide, N-[2-(1H-indol-3-yl)ethyl]cyclohexanamine (N-cyclohexyltryptamine), crystalline N-cyclohexyltryptamine, 2-(1H-in-dol-3-yl) ethanamine (tryptamine), crystalline tryptamine, N-[2-(1H-indol-3-yl)ethyl]cyclohexanamine hydrobromide (N-cyclohexyltryptamine hydrobromide), crystalline N-cyclohexyltryptamine hydrobromide, and specific crys-
(Continued)

talline forms thereof, including crystalline form 1 of 4-methylcarbonrato-DiPT chloride, crystalline form 1 of NiPT, crystalline form 1 of NiPT hydrobromide, crystalline form 1 of N-cyclohexyltryptamine, crystalline form 1 of tryptamine, and crystalline form 1 of N-cyclohexyltryptamine hydrobromide, to compositions containing the same, and to methods of treatment using them.

3 Claims, 15 Drawing Sheets

Related U.S. Application Data filed on Apr. 13, 2022, provisional application No. 63/330,467, filed on Apr. 13, 2022, provisional application No. 63/330,471, filed on Apr. 13, 2022, provisional application No. 63/330,468, filed on Apr. 13, 2022, provisional application No. 63/330,476, filed on Apr. 13, 2022.

(56) References Cited

FOREIGN PATENT DOCUMENTS

| | | | |
|---|---|---|---|
| WO | 2021/226416 | A1 | 11/2021 |
| WO | 2022/000091 | A1 | 1/2022 |
| WO | 2022/038299 | A1 | 2/2022 |
| WO | 2022/125616 | A1 | 6/2022 |

OTHER PUBLICATIONS

International Search Report and Written Opinion in International Application No. PCT/US2023/065718 dated Oct. 10, 2023.

Dolomanov, O. V., Bourhis, L. J., Gildea, R. J., Howard, J. A. K. & Puschmann, H. (2009). J. Appl. Cryst. 42, 339-341.

Sheldrick, G. M. (2015). Acta Cryst. C71, 3-8.

* cited by examiner

TRYPTAMINE DERIVATIVES

CROSS-REFERENCE TO RELATED APPLICATION

This application claims priority to U.S. Provisional Application No. 63/330,467, filed on Apr. 13, 2022; U.S. Provisional Application No. 63/330,468, filed on Apr. 13, 2022; U.S. Provisional Application No. 63/330,469, filed on Apr. 13, 2022; U.S. Provisional Application No. 63/330,471, filed on Apr. 13, 2022; U.S. Provisional Application No. 63/330,475, filed on Apr. 13, 2022; and U.S. Provisional Application No. 63/330,476, filed on Apr. 13, 2022; the disclosures of which are all incorporated by reference.

TECHNICAL FIELD

This disclosure relates to (2-{4-[(methoxycarbonyl)oxy]-1H-indol-3-yl}ethyl)bis(propan-2-yl)azanium chloride (4-methylcarbonato-N,N-diisopropyltryptramine chloride or 4-methylcarbonato-DiPT chloride), crystalline 4-methylcarbonato-DiPT chloride, and specific crystalline forms thereof, including crystalline form 1 of 4-methylcarbonato-DiPT chloride; to pharmaceutical compositions containing 4-methylcarbonato-DiPT chloride or crystalline 4-methylcarbonato-DiPT chloride, including crystalline form 1 of 4-methylcarbonato-DiPT chloride; and to methods of treatment/therapeutic uses of 4-methylcarbonato-DiPT chloride or crystalline 4-methylcarbonato-DiPT chloride, including crystalline form 1 of 4-methylcarbonato-DiPT chloride.

This disclosure further relates to [2-(1H-indol-3-yl)ethyl](propan-2-yl)amine (N-isopropyltryptamine or NiPT), crystalline NiPT, and specific crystalline forms thereof, including crystalline form 1 of NIPT; to pharmaceutical compositions containing NiPT or crystalline NIPT, including crystalline form 1 of NiPT; and to methods of treatment/therapeutic uses of NiPT or crystalline NiPT, including crystalline form 1 of NiPT.

This disclosure further relates to N-[2-(1H-indol-3-yl)ethyl]propan-2-amine hydrobromide (N-isopropyltryptamine hydrobromide or NiPT hydrobromide), crystalline NiPT hydrobromide, and specific crystalline forms thereof, including crystalline form 1 of NiPT hydrobromide; to pharmaceutical compositions containing crystalline NiPT hydrobromide, including crystalline form 1 of NiPT hydrobromide; and to methods of treatment/therapeutic uses of crystalline NiPT hydrobromide, including crystalline form 1 of NiPT hydrobromide.

This disclosure further relates to N-[2-(1H-indol-3-yl)ethyl]cyclohexanamine (N-cyclohexyltryptamine), crystalline N-cyclohexyltryptamine, and specific crystalline forms thereof, including crystalline form 1 of N-cyclohexyltryptamine; to pharmaceutical compositions containing crystalline N-cyclohexyltryptamine, including crystalline form 1 of N-cyclohexyltryptamine; and to methods of treatment/therapeutic uses of crystalline N-cydohexyltryptamine, including crystalline form 1 of N-cyclohexyltryptamine.

This disclosure further relates to 2-(1H-indol-3-yl)ethanamine (tryptamine), crystalline tryptamine, and specific crystalline forms thereof, induding crystalline form 1 of tryptamine; to pharmaceutical compositions containing tryptamine or crystalline tryptamine, including crystalline form 1 of tryptamine; and to methods of treatment/therapeutic uses of tryptamine or crystalline tryptamine, including crystalline form 1 of tryptamine.

This disclosure further relates to N-[2-(1H-indol-3-yl)ethyl]cyclohexanamine hydrobromide (N-cyclohexyltryptamine hydrobromide), crystalline N-cyclohexyltryptamine hydrobromide, and specific crystalline forms thereof, including crystalline form 1 of N-cyclohexyltryptamine hydrobromide; to pharmaceutical compositions containing N-cyclohexyltryptamine hydrobromide or crystalline N-cyclohexyltryptamine hydrobromide, including crystalline form 1 of N-cyclohexyltryptamine hydrobromide; and to methods of treatment/therapeutic uses of N-cyclohexyltryptamine hydrobromide or crystalline N-cyclohexyltryptamine hydrobromide, including crystalline form 1 of N-cyclohexyltryptamine hydrobromide.

BACKGROUND OF THE INVENTION

Obtaining specific salts or crystalline forms of an active pharmaceutical ingredient (API) is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process. Additionally, preparing a crystalline API and solving its crystal structure provides the gold standard for chemical characterization and determining the molecular formula (and molecular weight) of the API. Accordingly, preparing a crystalline form with an accompanying crystal structure thereof prevents potential ambiguities and/or inaccuracies in the API's molecular weight. This is important because the API's molecular weight is used to calculate the concentration of compositions comprising that API. Thus, inaccuracies in molecular weight may lead to errors in the calculations pertaining to dosing, potency, toxicity, etc. in all downstream in vitro and in vivo assays that correlated the concentration of the API with a measured property. Accordingly, there remains a need to obtain and characterize crystalline forms of APIs, such as tryptamines and other psychedelic drug compounds.

SUMMARY OF THE INVENTION

This disclosure relates to (2-{4-[(methoxycarbonyl)oxy]-1H-indol-3-yl}ethyl)bis(propan-2-yl)azanium chloride (4-methylcarbonato-N,N-diisopropyltryptramine chloride or 4-methylcarbonato-DiPT chloride), crystalline 4-methylcarbonato-DiPT chloride, and specific crystalline forms thereof. In one embodiment, this disclosure pertains to particular crystalline forms of 4-methylcarbonato-DiPT chloride, including crystalline form 1 of 4-methylcarbonato-DiPT chloride. In one embodiment, crystalline form 1 of 4-methylcarbonato-DiPT chloride is characterized by at least one of: a monoclinic, $P2_{1/n}$ space group at a temperature of about 297(2) K; unit cell dimensions a=13.3128(11) Å, b=7.8017(7) Å, c=18.9739(18) Å, α=90°, β=96.681(3)°, and γ=90°; an X-ray powder diffraction (XRPD) pattern substantially similar to FIG. 13; and an X-ray powder diffraction pattern characterized by at least two peaks selected from 7.7, 12.3, and 18.8 °2θ±0.2*2θ.

This disclosure further relates to [2-(1H-indol-3-yl)ethyl](propan-2-yl)amine (N-isopropyltryptamine or NiPT), crystalline NiPT, and specific crystalline forms thereof. In one embodiment, this disclosure pertains to particular crystalline forms of NiPT, including crystalline form 1 of NiPT. In one embodiment, crystalline form 1 of NiPT is characterized by at least one of: a monoclinic, Cc space group at a temperature of about 297(2) K; unit cell dimensions a=13.6490(12) Å, b=7.3196(6) Å, c=12.5727(10) Å, α=90°, β=109.285(3)°, and γ=90°; an X-ray powder diffraction (XRPD) pattern substantially similar to FIG. 14 and an X-ray powder diffraction pattern characterized by at least two peaks selected from 13.7, 18.7, and 22.1°2θ±2 0.2 °2θ.

This disclosure further relates to N-[2-(1H-indol-3-yl) ethyl]propan-2-amine hydrobromide (N-isopropyltryptamine hydrobromide or NiPT hydrobromide), crystalline NiPT hydrobromide, and specific crystalline forms thereof. In one embodiment, this disclosure pertains to particular crystalline forms of NiPT hydrobromide, including crystalline form 1 of NiPT hydrobromide. In one embodiment, crystalline form 1 of NiPT hydrobromide is characterized by at least one of: an orthorhombic, $P2_12_12_1$ space group at a temperature of about 297(2) K; unit cell dimensions a=5.9418(3) Å, b=10.4163(6) Å, c=22.3928(14) Å, α=90°, β=90°, and γ=90°; an X-ray powder diffraction (XRPD) pattern substantially similar to FIG. 15; and an X-ray powder diffraction pattern characterized by at least two peaks selected from 7.9, 9.4, and 19.1 ° 2θ±0.2 ° 2θ.

This disclosure further relates to N-[2-(1H-indol-3-yl) ethyl]cyclohexanamine (N-cyclohexyltryptamine), crystalline N-cyclohexyltryptamine, and specific crystalline forms thereof. In one embodiment, this disclosure pertains to particular crystalline forms of N-cyclohexyltryptamine, including crystalline form 1 of N-cyclohexyltryptamine. In one embodiment, crystalline form 1 of N-cyclohexyltryptamine is characterized by at least one of: a monoclinic, $P2_1$ space group at a temperature of about 297(2) K; unit cell dimensions a=8.5446(6) Å, b=10.3990(7) Å, c=8.6149(6) Å, α=90°, β=116.784(2)°, and γ=90°; an X-ray powder diffraction (XRPD) pattern substantially similar to FIG. 16; and an X-ray powder diffraction pattern characterized by at least two peaks selected from 14.3, 17.0, and 22.5 °2θ±0.2°2θ.

This disclosure further relates to 2-(1H-indol-3-yl) ethanamine (tryptamine), crystalline tryptamine, and specific crystalline forms thereof. In one embodiment, this disclosure pertains to particular crystalline forms of tryptamine, including crystalline form 1 of tryptamine. In one embodiment, crystalline form 1 of tryptamine is characterized by at least one of: an orthorhombic, $P2_12_12_1$ space group at a temperature of about 297(2) K; unit cell dimensions a=8.4953(6) Å, b=8.5431(7) Å, c=12.2965(8) Å, α=90°, β=90°, and γ=90°; an X-ray powder diffraction (XRPD) pattern substantially similar to FIG. 17; and an X-ray powder diffraction pattern characterized by at least two peaks selected from 16.4, 17.8, and 20.6 °2θ±0.2 °2θ.

This disclosure further relates to N-[2-(1H-indol-3-yl) ethyl]cyclohexanamine hydrobromide (N-cyclohexyltryptamine hydrobromide), crystalline N-cyclohexyltryptamine hydrobromide, and specific crystalline forms thereof. In one embodiment, this disclosure pertains to particular crystalline forms of N-cyclohexyltryptamine hydrobromide, including crystalline form 1 of N-cyclohexyltryptamine hydrobromide. In one embodiment, crystalline form 1 of N-cydohexyltryptamine hydrobromide is characterized by at least one of: a monoclinic, $P2_{1/n}$ space group at a temperature of about 297(2) K; unit cell dimensions a=10.5584(6) Å, b=7.9266(5) Å, c=19.4507(13) Å, α=90°, β=92.406(2)°, and γ=90°; an X-ray powder diffraction (XRPD) pattern substantially similar to FIG. 18; and an X-ray powder diffraction pattern characterized by at least two peaks selected from 12.0, 17.7, and 18.8°2θ±0.2°2θ.

The disclosure further relates to a composition comprising 4-methylcarbonato-DiPT chloride, crystalline 4-methylcarbonato-DiPT chloride, or specific crystalline forms thereof, such as crystalline form 1 of 4-methylcarbonato-DiPT chloride, and at least one excipient.

The disclosure further relates to a composition comprising NiPT, crystalline NiPT, or specific crystalline forms thereof, such as crystalline form 1 of NIPT, and at least one excipient.

The disclosure further relates to a composition comprising NiPT hydrobromide, crystalline NiPT hydrobromide, or specific crystalline forms thereof, such as crystalline form 1 of NiPT hydrobromide, and at least one excipient.

The disclosure further relates to a composition comprising N-cyclohexyltryptamine, crystalline N-cyclohexyltryptamine, or specific crystalline forms thereof, such as crystalline form 1 of N-cyclohexyltryptamine, and at least one excipient.

The disclosure further relates to a composition comprising tryptamine, crystalline tryptamine, or specific crystalline forms thereof, such as crystalline form 1 of tryptamine, and at least one excipient.

The disclosure further relates to a composition comprising N-cyclohexyltryptamine hydrobromide, crystalline N-cydohexyltryptamine hydrobromide, or specific crystalline forms thereof, such as crystalline form 1 of N-cyclohexyltryptamine hydrobromide, and at least one excipient.

The disclosure also provides a composition comprising4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide, as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone; and at least one excipient.

The disclosure also relates to a method of preventing or treating a psychological disorder comprising the step of administering to a subject in need thereof a therapeutically effective amount of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NIPT hydrobromide, crystalline form 1 of N-cyclohexyltryptamine, crystalline form 1 of tryptamine, or crystalline form 1 of N-cyclohexyltryptamine hydrobromide, or a composition according to this disclosure.

The disclosure further relates to a method of preventing or treating inflammation and/or pain, preventing or treating a neurological disorder, modulating activity of a mitogen-activated protein kinase (MAPK), modulating neurogenesis, or modulating neurite outgrowth comprising the step of administering to a subject in need thereof a therapeutically effective amount of a compound of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine), crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, and crystalline form 1 of N-cyclohexyltryptamine hydrobromide, and to administering a pharmaceutical composition or a composition according to the invention.

As used herein, the term "a subject in need thereof" refers to a person requiring a composition to treat a particular disease or condition (e.g., inflammation, pain, a psychological disorder, modulating activity at a receptor, etc.). In one embodiment, the "subject in need thereof" may be identified by analyzing, diagnosing, and/or determining whether the person (or subject) requires the composition for treatment of a particular disease or condition. In one embodiment, identifying a person in need of treatment comprises diagnosing a person with a medical condition, e.g., a neurological disorder, a chemical imbalance, a hereditary condition, etc. In one embodiment, identifying a person in need of treatment comprises performing a psychiatric evaluation. In one embodiment, identifying a person in need of treatment comprises performing a blood test. In one embodiment, identifying a person in need of treatment comprises determining whether a person has a compulsive disorder. In one embodiment, identifying a person in need of treatment comprises self-identifying as having a compulsive disorder.

DETAILED DESCRIPTION

Compounds

Figure 1:
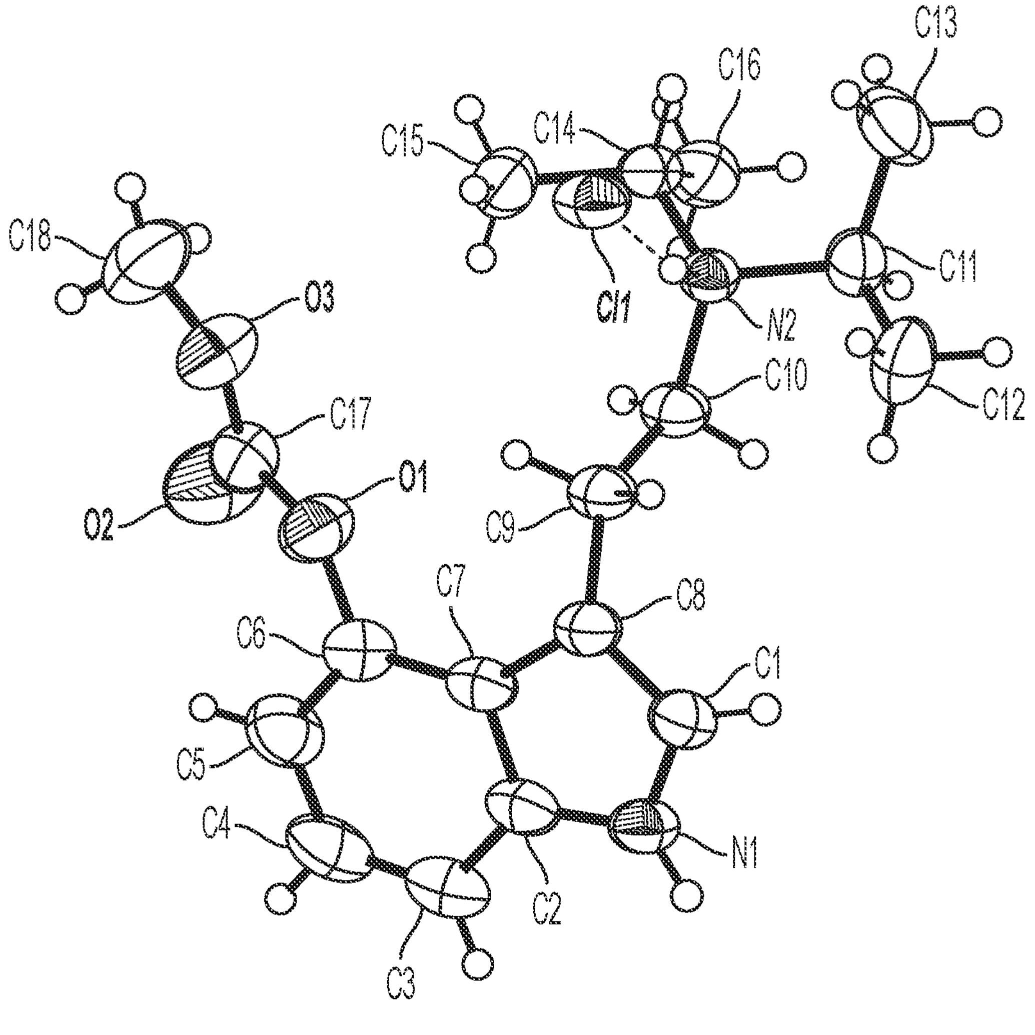
FIG. 1 shows the molecular structure of crystalline form 1 of 4-methylcarbonato-N,N-diisopropyltryptramine chloride.

This disclosure relates to (2-{4-[(methoxycarbonyl)oxy]-1H-indol-3-yl}ethyl)bis(propan-2-yl)azanium chloride (4-methylcarbonato-N,N-diisopropyltryptramine chloride or 4-methylcarbonato-DiPT chloride), crystalline 4-methylcarbonato-DiPT chloride, [2-(1H-indol-3-yl)ethyl](propan-2-yl)amine (N-isopropyltryptamine or NIPT), crystalline NIPT, N-[2-(1H-indol-3-yl)ethyl]propan-2-amine hydrobromide (N-isopropyltryptamine hydrobromide or NiPT hydrobromide), crystalline NiPT hydrobromide, N-[2-(1H-indol-3-yl)ethyl]cyclohexanamine (N-cydohexyltryptamine), crystalline N-cyclohexyltryptamine, 2-(1H-indol-3-yl) ethanamine (tryptamine), crystalline tryptamine, N-[2-(1H-indol-3-yl)ethyl]cyclohexanamine hydrobromide (N-cyclohexyltryptamine hydrobromide), crystalline N-cyclohexyltryptamine hydrobromide, and specific crystalline forms thereof, including crystalline form 1 of 4-methylcarbonato-DiPT chloride, crystalline form 1 of NIPT, crystalline form 1 of NIPT hydrobromide, crystalline form 1 of N-cyclohexyltryptamine, crystalline form 1 of tryptamine, and crystalline form 1 of N-cyclohexyltryptamine hydrobromide; to pharmaceutical compositions containing 4-methylcarbonato-DiPT chloride, crystalline 4-methylcarbonato-DiPT chloride (including crystalline form 1 of 4-methylcarbonato-DiPT chloride), NiPT, crystalline NiPT (including crystalline form 1 of NiPT), NiPT hydrobromide, crystalline NiPT hydrobromide (including crystalline form 1 of NiPT hydrobromide), N-cyclohexyltryptamine, crystalline N-cyclohexyltryptamine (including crystalline form 1 of N-cyclohexyltryptamine), tryptamine, crystalline tryptamine (including crystalline form 1 of tryptamine), N-cyclohexyltryptamine hydrobromide, or crystalline N-cyclohexyltryptamine hydrobromide (including crystalline form 1 of N-cyclohexyltryptamine hydrobromide) according to the disclosure. The therapeutic uses of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, and crystalline form 1 of N-cyclohexyltryptamine hydrobromide according to the disclosure are described below as well as compositions containing them. 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, and crystalline form 1 of N-cyclohexyltryptamine hydrobromide, and some exemplary methods used to characterize it are described below.

4-methylcarbonato-DiPT chloride has the following chemical formula:

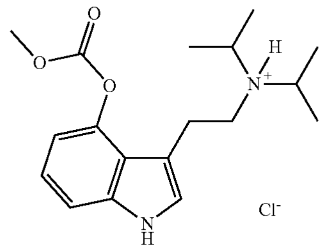

NiPT has the following chemical formula:

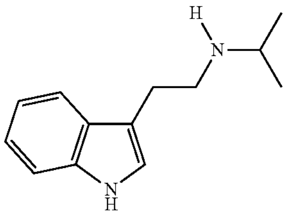

NiPT hydrobromide has the following chemical formula:

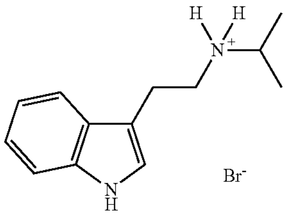

N-cyclohexyltryptamine has the following chemical formula:

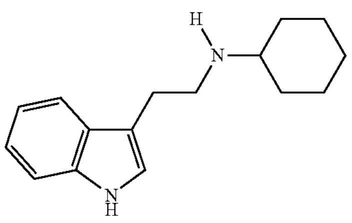 [SMILES: c1ccc2c(CCNC3CCCCC3)c[nH]c2c1]

Tryptamine has the following chemical formula:

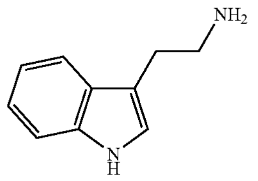 [SMILES: NCCc1c[nH]c2ccccc12]

N-cyclohexyltryptamine hydrobromide has the following chemical formula:

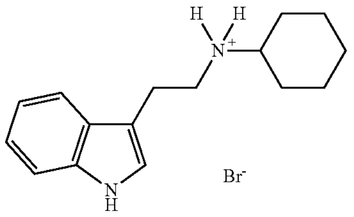

Methods of Treatment and Therapeutic Uses 4-methylcarbonato-DiPT chloride, crystalline 4-methylcarbonato-DiPT chloride (such as crystalline form 1 of 4-methylcarbonato-DiPT chloride), NiPT, crystalline NiPT (such as crystalline form 1 of NiPT), NiPT hydrobromide, crystalline NiPT hydrobromide (such as crystalline form 1 of NiPT hydrobromide), N-cyclohexyltryptamine, crystalline N-cyclohexyltryptamine (such as crystalline form 1 of N-cyclohexyltryptamine), tryptamine, crystalline tryptamine (such as crystalline form 1 of tryptamine), N-cyclohexyltryptamine hydrobromide, or crystalline N-cyclohexyltryptamine hydrobromide (such as crystalline form 1 of N-cyclohexyltryptamine hydrobromide) according to the disclosure, and the methods and the compositions (e.g., pharmaceutical compositions) are used to regulate the activity of a neurotransmitter receptor by administering a therapeutically effective dose of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyciohexyltryptamine, tryptamine, crystalline tryptamine, N-cyclohexyltryptamine hydrobromide, crystalline N-cyciohexyltryptamine hydrobromide, or specific crystalline forms thereof, such as crystalline form 1 of 4-methylcarbonato-DIPT chloride, crystalline form 1 of NIPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure. In one embodiment, 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide according to the disclosure, and the methods and the compositions (e.g., pharmaceutical compositions)

are used to treat inflammation and/or pain by administering a therapeutically effective dose of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure.

Methods of the disclosure also relate to the administration of a therapeutically effective amount of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide to prevent or treat a disease or condition, such as those discussed below for a subject in need of treatment. 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NIPT, crystalline form 1 of NIPT hydrobromide, crystalline form 1 of N-cyclohexyltryptamine, crystalline form 1 of tryptamine, or crystalline form 1 of N-cyclohexyltryptamine hydrobromide may be administered neat or as a composition comprising 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide as discussed below.

4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used to prevent and/or treat a psychological disorder. The disclosure provides a method for preventing and/or treating a psychological disorder by administering to a subject in need thereof a therapeutically effective amount of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NIPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure, including the exemplary embodiments discussed herein. The psychological disorder may be chosen from: depression; psychotic disorder; schizophrenia; schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); shared psychotic disorder (shared paranoia disorder); brief psychotic disorder (other and unspecified reactive psychosis); psychotic disorder not otherwise specified (unspecified psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome; post-traumatic stress disorder (PTSD); premenstrual dysphoric disorder (PMDD); and premenstrual syndrome (PMS).

4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used to prevent and/or treat a brain disorder. The disclosure provides a method for preventing and/or treating a brain disorder (e.g., Huntington's disease, Alzheimer's disease, dementia, and Parkinson's disease) by administering to a subject in need thereof a therapeutically effective amount of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide.

4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide including the exemplary embodiments discussed above.

4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure, induding the exemplary embodiments discussed herein. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e., mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NIPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used to modulate activity of a mitogen-activated protein kinase (MAPK), comprising administering a composition of the invention. MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-a. In the central nervous system, p38-alpha regulates neuronal death and neurite degeneration, and it is a common target of Alzheimer's disease therapies. JNK3 is a neuronal-specific protein isoform of the JNKs. It is involved with the regulation of apoptosis. JNK3 also plays a role in modulating the response of cytokines, growth factors, and oxidative stress.

As used herein, the term "modulating activity of a mitogen-activated protein kinase" refers to changing, manipulating, and/or adjusting the activity of a mitogen-activated protein kinase. In one embodiment, modulating the activity of a MAPK can influence neural health, neurogenesis, neural growth and differentiation, and neurodegenerative diseases.

4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used to modulate neurogenesis, comprising administering a composition of the invention. As used herein, the term "modulating neurogenesis" refers to changing, manipulating, and/or adjusting the growth and development of neural tissue. In one embodiment, neurogenesis comprises adult neurogenesis, in which new neural stem cells are generated from neural stem cells in an adult animal. In one embodiment, modulating neurogenesis comprises increasing and/or enhancing the rate at which new neural tissue is developed.

4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used to modulate neurite outgrowth, comprising administering a composition of the invention. As used herein, the term "modulating neurite outgrowth" refers to changing, manipulating, and/or adjusting the growth and development of neural projections, or "neurites." In one embodiment, neurogenesis comprises modulating the growth of new neurites, the number of neurites per neuron, and/or neurite length. In one embodiment, modulating neurite outgrowth comprises increasing and/or enhancing the rate and/or length at which neurites develop.

4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used to prevent and/or treat sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used to prevent and/or treat women's health disorders including, but not limited to, menstrual cramping, dysmenorrhea, post-hysterectomy pain, vaginal or vulvar vestibule mucosa disorder, menopausal-related disorders, vaginal atrophy, or vulvar vestibulitis.

Compositions

The disclosure also relates to compositions comprising an effective amount of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide and an excipient (e.g., a pharmaceutically-acceptable excipient). In another embodiment, the disclosure also relates to pharmaceutical compositions comprising a therapeutically effective amount of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide and a pharmaceutically acceptable excipient (also known as a pharmaceutically acceptable carrier). As discussed above, 4-methylcarbonato-DiPT chloride, crystalline 4-methylcarbonato-DIPT chloride, NIPT, crystalline NIPT, NIPT hydrobromide, crystalline NIPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be, for example, therapeutically useful to prevent and/or treat the psychological disorders, brain disorders, pain, and inflammation as well as the other disorders described herein.

A composition or a pharmaceutical composition of the disdosure may be in any form which contains 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide. The composition may be, for example, a tablet, capsule, liquid suspension, injectable, topical, or transdermal. The compositions generally contain, for example, about 1% to about 99% by weight of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NIPT, crystalline form 1 of NIPT hydrobromide, crystalline form 1 of N-cyclohexyltryptamine, crystalline form 1 of tryptamine, or crystalline form 1 of N-cyclohexyltryptamine hydrobromide of the disclosure and, for example, 99% to 1% by weight of at least one suitable pharmaceutically acceptable excipient. In one embodiment, the composition may be between about 5% and about 75% by weight of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NIPT, crystalline form 1 of NIPT hydrobromide, crystalline form 1 of N-cyclohexyltryptamine, crystalline form 1 of tryptamine, or crystalline form 1 of N-cyclohexyltryptamine hydrobromide of the disclosure, with the rest being at least one suitable pharmaceutically acceptable excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NIPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used as the "first purified psilocybin derivative" in the compositions described in US 2018/0221396 A1 and US 2019/0142851 A1. Accordingly, this disclosure provides a composition comprising: a first component comprising 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NIPT hydrobromide, crystalline form 1 of N-cyclohexyltryptamine, crystalline form 1 of tryptamine, or crystalline form 1 of N-cyclohexyltryptamine hydrobromide of the disclosure; at least one second component selected from at least one of (a) a serotonergic drug, (b) a purified psilocybin derivative, (c) a purified cannabinoid, and (d) a purified terpene; and at least one pharmaceutically-acceptable excipient or at least one other adjuvant. Such a composition may be a pharmaceutical composition wherein the components are present individually in therapeutically effective amounts or by combination in a therapeutically effective amount to treat a disease, disorder, or condition as described herein.

When used in such compositions as a first component comprising 4-methylcarbonato-DiPT chloride, crystalline 4-methylcarbonato-DiPT chloride, NiPT, crystalline NiPT, NiPT hydrobromide, crystalline NIPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure with a second component selected from at least one of (a) a serotonergic drug, (b) a purified psilocybin derivative, (c) a purified cannabinoid, and (d) a purified terpene, the compositions represent particular embodiments of the invention. Compositions having as a first component 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NIPT, crystalline form 1 of NIPT hydrobromide, crystalline form 1 of N-cyclohexyltryptamine, crystalline form 1 of tryptamine, or crystalline form 1 of N-cyclohexyltryptamine hydrobromide of the disclosure with a second component selected from at least one of (e) an adrenergic drug, (f) a dopaminergic drug, (g) a monoamine oxidase inhibitor, (h) a purified erinacine, and (i) a purified hericenone represent additional particular embodiments of the invention represented by the compositions having 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cydohexyltryptamine hydrobromide, or specific crystalline forms thereof, such as crystalline form 1 of 4-methylcarbonato-DiPT chloride, crystalline form 1 of NiPT, crystalline form 1 of NIPT hydrobromide, crystalline form 1 of N-cyclohexyltryptamine, crystalline form 1 of tryptamine, or crystalline form 1 of N-cyclohexyltryptamine hydrobromide according to the disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

Within the context of this disclosure, the term "purified" means separated from other materials, such as plant or fungal material, e.g., protein, chitin, cellulose, or water. In one embodiment, the term "purified" refers to a compound substantially free of other materials. In one embodiment, the term "purified" refers to a compound that is substantially free from a second tryptamine compound. In one embodiment, the term "purified" refers to a compound substantially free from histidine. In one embodiment, the term "purified" refers to a compound substantially free from a biological material, such as mold, fungus, plant matter, or bacteria. In one embodiment, the term "purified" refers to a compound substantially free from a paralytic.

In one embodiment, the term "purified" refers to a compound which has been separated from other compounds that are typically co-extracted when the purified compound is extracted from a naturally occurring organism. In one embodiment, a "purified" psilocybin derivative is partially or completely isolated from other psilocybin derivatives present in a source material, such as a psilocybin-containing mushroom. In one example, "purified" baeocystin is substantially free from psilocybin and/or psilocin. By contrast, traditional psilocybin mushroom extracts (aka crude extracts or fruit body extracts) would be expected to contain an unpredictable and varying amount of psilocybin, psilocin, baeocystin, norbaeocystin, salts thereof, or combinations thereof. Other examples of unpurified psilocybin derivatives would include mycelium containing psilocybin derivatives and/or naturally occurring fungal material such as biological material and/or structural material such as chitin. Similarly, the term "*cannabis* extracts" or "cannabinoid extracts" traditionally refers to whole plants (aka crude or full spectrum extracts) which have not been subjected to further purification to eliminate unwanted molecules that naturally occur in the *cannabis* plant. For example, a "*cannabis* extract comprising cannabidiol" could be expected to include cannabidiol (aka "CBD") and also varying amounts of other compounds, including cannabinoids, terpenes, and other biological material.

In one embodiment, the term "purified" refers to a compound or composition that has been crystallized.

In one embodiment, the term "purified" refers to a compound or composition that has been chromatographed, for example by gas chromatography, liquid chromatography (e.g., LC, HPLC, etc.), etc.

In one embodiment, the term "purified" refers to a compound or composition that has been distilled.

In one embodiment, the term "purified" refers to a compound or composition that has been sublimed.

In one embodiment, the term "purified" refers to a compound or composition that has been subject to two or more steps chosen from crystallization, chromatography, distillation, or sublimation.

In one embodiment, the term "purified" refers to a compound that is between 80-100% pure.

In one embodiment, the term "purified" refers to a compound that is between 90-100% pure.

In one embodiment, the term "purified" refers to a compound that is between 95-100% pure.

In one embodiment, the term "purified" refers to a compound that is between 99-100% pure.

In one embodiment, the term "purified" refers to a compound that is between 99.9-100% pure.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments. Exemplary psilocybin derivatives include but are not limited to psilocybin itself and the psilocybin derivatives described in paragraphs [0081]-[0109] of US 2018/0221396 A1 and [0082]-[0110] US 2019/0142851 A1 as well as the disclosed exemplary embodiments. Exemplary cannabinoids include but are not limited to the cannabinoids described in paragraphs [0111]-[0145] of US 2018/0221396 A1 and [0112]-[0146] US 2019/0142851 A1 as well as the disclosed exemplary embodiments. Exemplary terpenes include but are not limited to the terpenes described in paragraphs [0160]-[0238] of US 2018/0221396 A1 and [0161]-[0300] US 2019/0142851 A1 as well as the disclosed exemplary embodiments.

A pharmaceutical formulation of the disclosure may comprise, consist essentially of, or consist of (a) 4-methylcarbonato-DIPT chloride, crystalline 4-methylcarbonato-DIPT chloride, NIPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone, and (c) a pharmaceutically acceptable excipient. In some embodiments, 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide and the second active compound(s) are each present in a therapeutically effective amount using purposefully engineered and unnaturally occurring molar ratios. Exemplary molar ratios of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing 4-methylcarbonato-DiPT chloride, crystalline 4-methylcarbonato-DiPT chloride, NiPT, crystalline NiPT, NIPT hydrobromide, crystalline NIPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure and a serotonergic drug, a purified psilocybin derivative, a purified cannabinoid, or a purified terpene, each present in a therapeutically effective amount using purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. According to this disclosure composition containing 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cydohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be used in place of a "purified psilocybin derivative" in the compositions described in US 2018/0221396 A1 and US 2019/0142851 A1. Accordingly, the disclosure provides a pharmaceutical formulation comprising as (a) 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure and at least one second component selected from (a) a purified psilocybin derivative, (b) a purified cannabinoid, and (c) a purified terpene; and at least one pharmaceutically-acceptable excipient or at least one other adjuvant, as described herein. Such a composition may be a pharmaceutical composition wherein the components are present individually in therapeutically effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments. Some exemplary serotonergic drugs include SSRIs and SNRIs. Some examples of specific serotonergic drugs include the following molecules, including any salts, solvates, or polymorphs thereof: 6-allyl-N,N-diethyl-NL; N,N-dibutyl-T; N,N-diethyl-T; N,N-diisopropyl-T; 5-methyoxy-alpha-methyl-T; N,N-dimethyl-T; 2,alpha-dimethyl-T; alpha,N-dimethyl-T; N,N-dipropyl-T; N-ethyl-N-isopropyl-T; alpha-ethyl-T; 6-N,N-Triethyl-NL; 3,4-dihydro-7-methoxy-1-methyl-C; 7-methyoxy-1-methyl-C; N,N-dibutyl-4-hydroxy-T; N,N-diethyl-4-hydroxy-T; N,N-diisopropyl-4-hydroxy-T; N,N-dimethyl-4-hydroxy-T; N,N-dimethyl-5-hydroxy-T; N, N-dipropyl-4-hydroxy-T; N-ethyl-4-hydroxy-N-methyl-T; 4-hydroxy-N-Isopropyl-N-methyl-T; 4-hydroxy-N-methyl-N-propyl-T; 4-hydroxy-N, N-tetramethylene-T; ibogaine; N,N-diethyl-L; N-butyl-N-methyl-T; N,N-diisopropyl-4,5-methylenedioxy-T; N,N-diisopropyl-5,6-methylenedioxy-T; N,N-dimethyl-4,5-methylenedioxy-T; N,N-dimethyl-5,6-methylenedioxy-T; N-isopropyl-N-methyl-5,6-methylenedioxy-T; N,N-diethyl-2-methyl-T; 2-N,N-trimethyl-T; N-acetyl-5-methoxy-T; N,N-diethyl-5-methoxy-T; N,N-diisopropyl-5-methoxy-T; 5-methoxy-N,N-dimethyl-T; N-isopropyl-4-methoxy-N-methyl-T; N-isopropyl-5-methoxy-N-methyl-T; 5,6-dimethoxy-N-isopropyl-N-methyl-T; 5-methoxy-N-methyl-T; 5-methoxy-N,N-tetramethylene-T; 6-methoxy-1-methyl-1,2,3,4-tetrahydro-C; 5-methoxy-2-N,N-trimethyl-T; N,N-dimethyl-5-methylthio-T; N-isopropyl-N-methyl-T; alpha-methyl-T; N-ethyl-T; N-methyl-T; 6-propyl-N L; N,N-tetramethylene-T; tryptamine; 7-methoxy-1-methyl-1,2,3,4-tetrahydro-C; and alpha,N-dimethyl-5-methoxy-T. For additional information regarding these compounds see Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinold, chlordlazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In an exemplary embodiment, the serotonergic drug is 3,4-methylenedioxymethamphetamine.

Exemplary psilocybin derivatives include but are not limited to psilocybin itself and the psilocybin derivatives described in paragraphs [0081]-[0109] of US 2018/0221396 A1 and [0082]-[0110] US 2019/0142851 A1 as well as the disclosed exemplary embodiments, incorporated here by reference. In one embodiment, the compositions disclosed herein comprise one or more purified psilocybin derivatives chosen from: [3-(2-dimethylaminoethyl)-1H-indol-4-yl]dihydrogen phosphate; 4-hydroxytryptamine; 4-hydroxy-N,N-dimethyltryptamine; [3-(2-methylaminoethyl)-1H-indol-4-yl]dihydrogen phosphate; 4-hydroxy-N-methyltryptamine; [3-(aminoethyl)-1H-indol-4-yl] dihydrogen phosphate; [3-(2-trimethylaminoethyl)-1H-indol-4-yl]dihydrogen phosphate; and 4-hydroxy-N,N,N-trimethyltryptamine.

Exemplary cannabinoids include but are not limited to the cannabinoids described in paragraphs [0111]-[0145] of US 2018/0221396 A1 and [0112]-[0146] US 2019/0142851 A1 as well as the disclosed exemplary embodiments. Examples of cannabinoids within the context of this disclosure include the following molecules: cannabichromene (CBC); cannabichromenic acid (CBCA); cannabichromevarin (CBCV); cannabichromevarinic acid (CBCVA); cannabicyclol (CBL); cannabicyclolic acid (CBLA); cannabicyclovarin (CBLV); cannabidiol (CBD); cannabidiol monomethylether (CBDM); cannabidiolic acid (CBDA); cannabidiorcol (CBD-C1); cannabidivarin (CBDV); cannabidivarinic acid (CBDVA); cannabielsoic acid B (CBEA-B); cannabielsoin (CBE); cannabielsoin acid A (CBEA-A); cannabigerol (CBG); cannabigerol monomethylether (CBGM); cannabigerolic acid (CBGA); cannabigerolic acid monomethylether (CBGAM); cannabigerovarin (CBGV); cannabigerovarinic acid (CBGVA); cannabinodiol (CBND); cannabinodivarin (CBVD); cannabinol (CBN); cannabinol methylether (CBNM); cannabinol-C2 (CBN-C2); cannabinol-C4 (CBN-C4); cannabinolic acid (CBNA); cannabiorcol (CBN-C1); cannabivarin (CBV); cannabitriol (CBT); cannabitriolvarin (CBTV); 10-ethoxy-9-hydroxy-delta-6a-tetrahydrocannabinol; cannabicitran (CBTC); cannabiripsol (CBR); 8,9-dihydroxy-delta-6a-tetrahydrocannabinol; delta-8-tetrahydrocannabinol (A8-THC); delta-8-tetrahydrocannabinolic acid (A8-THCA); delta-9-tetrahydrocannabinol (THC); delta-9-tetrahydrocannabinol-C4 (THC-C4); delta-9-tetrahydrocannabinolic acid A (THCA-A); delta-9-tetrahydrocannabinolic acid B (THCA-B); delta-9-tetrahydrocannabinolic acid-C4 (THCA-C4); delta-9-tetrahydrocannabiorcol (THC-C1); delta-9-tetrahydrocannabiorcolic acid (THCA-C1); delta-9-tetrahydrocannabivarin (THCV); delta-9-tetrahydrocannabivarinic acid (THCVA); 10-oxo-delta-6a-tetrahydrocannabinol (OTHC); cannabichromanon (CBCF); cannabifuran (CBF); cannabiglendol; delta-9-cis-tetrahydrocannabinol (cis-THC); trihydroxy-delta-9-tetrahydrocannabinol (triOH-THC); dehydrocannabifuran (DCBF); and 3,4,5,6-tetrahydro-7-hydroxy-alpha-alpha-2-trimethyl-9-n-propyl-2,6-methano-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBVD, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed exemplary embodiments. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, lonone, Ipsdienol, Isoamyl acetate, Isoamyl alcohol, Isoamyl formate, isobomeol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isobomeol, limonene, linalool, menthol, myrcene, nerolidol, ocimene, phellandrene, phytol, pinene, pulegone, sabinene, terpineol, terpinolene, or valencene.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant. In one embodiment, an adrenergic drug is a norepinephrine transporter inhibitor. In one embodiment, an adrenergic drug is a vesicular monoamine transporter inhibitor. In one embodiment, an adrenergic drug is chosen from adrenaline, agmatine, amoxapine, aptazapine, atomoxetine, bupropion, clonidine, doxepin, duloxetine, esmirtazpine, mianserin, ketanserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor. In one embodiment, a dopaminergic drug is a vesicular monoamine transporter inhibitor. In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencydidine, phenethylamine, phenmetrazine, pimozide, piribedil, a psychostimulant, reserpine, risperidone, ropinirole, tetrabenazine, or thioridazine.

As used herein, the term "monoamine oxidase inhibitor" (MAOI) refers to a compound that blocks the actions of monoamine oxidase enzymes. In one embodiment, a MAOI inhibits the activity of one or both monoamine oxidase A and monoamine oxidase B. In one embodiment a MAOI is a reversible inhibitor of monoamine oxidase A. In one embodiment a MAOI is a drug chosen from isocarboxazid, phenelzine, or tranylcypromine. In one embodiment, a MAOI is β-carboline, pinoline, harmane, harmine, harmaline, harmalol, tetrahydroharmine, 9-methyl-β-carboline, or 3-carboxy-tetrahydrononharman.

In one embodiment, the compositions and methods disclosed herein include one or more purified erinacine molecules. In one embodiment, the compositions and methods disclosed herein comprise purified erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D. In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine J. In one embodiment, the compositions and methods disclosed herein comprise erinacine K In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S.

In one embodiment, the compositions and methods disclosed herein include one or more purified hericenone molecules. In one embodiment, the compositions and methods disclosed herein comprise purified hericenone A. In one embodiment, the compositions and methods disclosed herein comprise purified hericenone B. In one embodiment, the compositions and methods disclosed herein comprise purified hericenone C. In one embodiment, the compositions and methods disclosed herein comprise purified hericenone D. In one embodiment, the compositions and methods disclosed herein comprise purified hericenone E. In one embodiment, the compositions and methods disclosed herein comprise purified hericenone F. In one embodiment, the compositions and methods disclosed herein comprise purified hericenone G. In one embodiment, the compositions and methods disclosed herein comprise purified hericenone H.

Exemplary compositions of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone in exemplary molar ratios are shown in Table 1. 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, orspecific crystalline-forms thereof, such as crystalline form 1 of 4-methylcarbonato-DiPTchloride, crystalline form 1 of NiPT, crystalline form 1 of NiPT hydrobromide, crystalline form 1 of N-cyclohexyltryptamine, crystallineform 1 of tryptamine, or crystalline form 1 of N-cyclohexyltryptamne hydrobromide of the disclosure may be anyone of the exemplary embodiments described above including the crystalline forms as disclosed herein.

TABLE 1

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| 3,4-methylenedioxymethamphetamine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Citalopram | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Escitalopram | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Fluoxetine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Paroxetine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Sertraline | About 1:100 to about | About 1:100 to about | About 1:100 to about | About 1:100 to about | About 1:100 to about | About 1:100 to about |

TABLE 1-continued

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| | 100:1 | 100:1 | 100:1 | 100:1 | 100:1 | 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Duloxetine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| [3-(2-dimethylaminoethyl)-1H-indol-4-yl] dihydrogen phosphate | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| 4-hydroxytryptamine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| 4-hydroxy-N,N-dimethyltryptamine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| [3-(2-methylaminoethyl)-1H-indol-4-yl] dihydrogen phosphate | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |

TABLE 1-continued

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| 4-hydroxy-N-methyltryptamine | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 |
| [3-(aminoethyl)-1H-indol-4-yl] dihydrogen phosphate | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 |
| [3-(2-trimethylaminoethyl)-1H-indol-4-yl] dihydrogen phosphate | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 |
| 4-hydroxy-N,N,N-trimethyltryptamine | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 |
| THC | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 | About 1:5 to about 5:1 About 1:100 to about 100:1 About 1:25 to about 25:1 |
| CBC | About 1:5 to about 5:1 About 1:100 to about | About 1:5 to about 5:1 About 1:100 to about | About 1:5 to about 5:1 About 1:100 to about | About 1:5 to about 5:1 About 1:100 to about | About 1:5 to about 5:1 About 1:100 to about | About 1:5 to about 5:1 About 1:100 to about |

TABLE 1-continued

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| | 100:1 | 100:1 | 100:1 | 100:1 | 100:1 | 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| CBD | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| CBG | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Myrcene | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Pinene | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Caryophyllene | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |

TABLE 1-continued

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| Limonene | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 |
| Humulene | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 |
| Linalool | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 |
| Adrenaline | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 |
| Amineptine | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 | About 1:5 to about 5:1<br>About 1:100 to about 100:1<br>About 1:25 to about 25:1 |
| Erinacine A | About 1:5 to about 5:1<br>About 1:100 to about | About 1:5 to about 5:1<br>About 1:100 to about | About 1:5 to about 5:1<br>About 1:100 to about | About 1:5 to about 5:1<br>About 1:100 to about | About 1:5 to about 5:1<br>About 1:100 to about | About 1:5 to about 5:1<br>About 1:100 to about |

TABLE 1-continued

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| | 100:1 | 100:1 | 100:1 | 100:1 | 100:1 | 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Hericenone A | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Phenelzine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |

Exemplary pharmaceutical compositions of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone and an excipient with exemplary molar ratios of 4-methyicarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide to the second compound are shown in Table 2. 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be any one of the exemplary embodiments described above including the crystalline forms as disclosed herein.

TABLE 2

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| 3,4-methylenedioxymethamphetamine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Citalopram | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Escitalopram | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Fluoxetine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Paroxetine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Sertraline | About 1:100 to about | About 1:100 to about | About 1:100 to about | About 1:100 to about | About 1:100 to about | About 1:100 to about |

TABLE 2-continued

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| | 100:1 | 100:1 | 100:1 | 100:1 | 100:1 | 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Duloxetine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| [3-(2-dimethylaminoethyl)-1H-indol-4-yl] dihydrogen phosphate | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| 4-hydroxytryptamine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| 4-hydroxy-N,N-dimethyltryptamine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| [3-(2-methylaminoethyl)-1H-indol-4-yl] dihydrogen phosphate | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |

TABLE 2-continued

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| 4-hydroxy-N-methyltryptamine | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| [3-(aminoethyl)-1H-indol-4-yl] dihydrogen phosphate | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| [3-(2-trimethylaminoethyl)-1H-indol-4-yl] dihydrogen phosphate | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| 4-hydroxy-N,N,N-trimethyltryptamine | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| THC | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| CBC | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 | About 1:100 | About 1:100 | About 1:100 | About 1:100 | About 1:100 |

TABLE 2-continued

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| | to about 100:1 | to about 100:1 | to about 100:1 | to about 100:1 | to about 100:1 | to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| CBD | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| CBG | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Myrcene | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Pinene | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Caryophyllene | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about | About 1:25 to about | About 1:25 to about | About 1:25 to about | About 1:25 to about | About 1:25 to about |

TABLE 2-continued

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| | 25:1 | 25:1 | 25:1 | 25:1 | 25:1 | 25:1 |
| Limonene | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| Humulene | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| Linalool | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| Adrenaline | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| Amineptine | About 1:5 to about 5:1 | About 1:5 to about 5:1 | About 1:5 to about 5:1 | About 1:5 to about 5:1 | About 1:5 to about 5:1 | About 1:5 to about 5:1 |
| | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |

TABLE 2-continued

| Second Compound | Molar ratio of 4-methylcarbonato-DiPT chloride or crystalline 4-methylcarbonato-DiPT chloride, such as crystalline form 1 of 4-methylcarbonato-DiPT chloride:second compound | Molar ratio of NiPT or crystalline NiPT, such as crystalline form 1 of NiPT:second compound | Molar ratio of NiPT hydrobromide or crystalline NiPT hydrobromide, such as crystalline form 1 of NiPT hydrobromide:second compound | Molar ratio of N-cyclohexyltryptamine or crystalline N-cyclohexyltryptamine, such as crystalline form 1 of N-cyclohexyltryptamine:second compound | Molar ratio of tryptamine or crystalline tryptamine, such as crystalline form 1 of tryptamine:second compound | Molar ratio of N-cyclohexyltryptamine hydrobromide or crystalline N-cyclohexyltryptamine hydrobromide, such as crystalline form 1 of N-cyclohexyltryptamine hydrobromide:second compound |
|---|---|---|---|---|---|---|
| Erinacine A | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Hericenone A | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |
| Phenelzine | About 1:100 to about 100:1 | About 1:100 to about 100:1 | About 1:100 to about 100:1 | About 1:100 to about 100:1 | About 1:100 to about 100:1 | About 1:100 to about 100:1 |
| | About 1:25 to about 25:1 | About 1:25 to about 25:1 | About 1:25 to about 25:1 | About 1:25 to about 25:1 | About 1:25 to about 25:1 | About 1:25 to about 25:1 |
| | About 1:5 to about 5:1 | About 1:5 to about 5:1 | About 1:5 to about 5:1 | About 1:5 to about 5:1 | About 1:5 to about 5:1 | About 1:5 to about 5:1 |

An "effective amount" or a "therapeutically effective amount" of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure is generally in the range of about 0.1 to about 100 mg daily (oral dose), of about 0.1 to about 50 mg daily (oral dose), of about 0.25 to about 25 mg daily (oral dose), of about 0.1 to about 5 mg daily (oral dose), or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L Limbird, eds., McGraw-Hill Press, 155-173 (2001), which is incorporated herein by reference. 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure and pharmaceutical compositions containing it may be used in combination with other agents that are generally administered to a patient being treated for psychological and other disorders discussed above. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Exemplary carriers include those that do not substantially alter the structure or activity of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure, or produce undesirable biological effects or otherwise interact in a deleterious manner with any other component(s) of the pharmaceutical composition.

The pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. In some embodiments, the excipient is not water. In some embodiments, the excipient is not a solvent (e.g., EtOH, diethyl ether, ethyl acetate, or hydrocarbon-based solvents (e.g., hexanes). In some embodiments, the dosage form is substantially free of water and/or solvents, for example less than about 5% water by mass, less than 2% water by mass, less than 1% water by mass, less than 0.5% water by mass, or less than 0.1% water by mass.

Excipients or pharmaceutically acceptable adjuvants known in the pharmaceutical formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of 4-methylcarbonato-DiPT chloride, crystalline 4-methylcarbonato-DiPT chloride, NiPT, crystalline NiPT, NiPT hydrobromide, crystalline NiPT hydrobromide, N-cyclohexyltryptamine, crystalline N-cyclohexyltryptamine, tryptamine, crystalline tryptamine, N-cyclohexyltryptamine hydrobromide, crystalline N-cyclohexyltryptamine hydrobromide, or specific crystalline forms thereof, such as crystalline form 1 of 4-methylcarbonato-DiPT chloride, crystalline form 1 of NiPT, crystalline form 1 of NiPT hydrobromide, crystalline form 1 of N-cyclohexyltryptamine, crystalline form 1 of tryptamine, or crystalline form 1 of N-cyclohexyltryptamine hydrobromide of the disclosure in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

Exemplary Embodiments of the Invention

E1. (2-{4-[(methoxycarbonyl)oxy]-1H-indol-3-yl}ethyl) bis(propan-2-yl)azanium chloride (4-methylcarbonato-N,N-diisopropyltryptamine chloride).

E2. Crystalline (2-{4-[(methoxycarbonyl)oxy]-1H-indol-3-yl}ethyl)bis(propan-2-yl)azanium chloride (4-methylcarbonato-N,N-diisopropyltryptamine chloride).

E3. Crystalline form 1 of (2-{4-[(methoxycarbonyl)oxy]-1H-indol-3-yl}ethyl)bis(propan-2-yl)azanium chloride (4-methylcarbonato-N,N-diisopropyltryptamine chloride).

Figure 13:
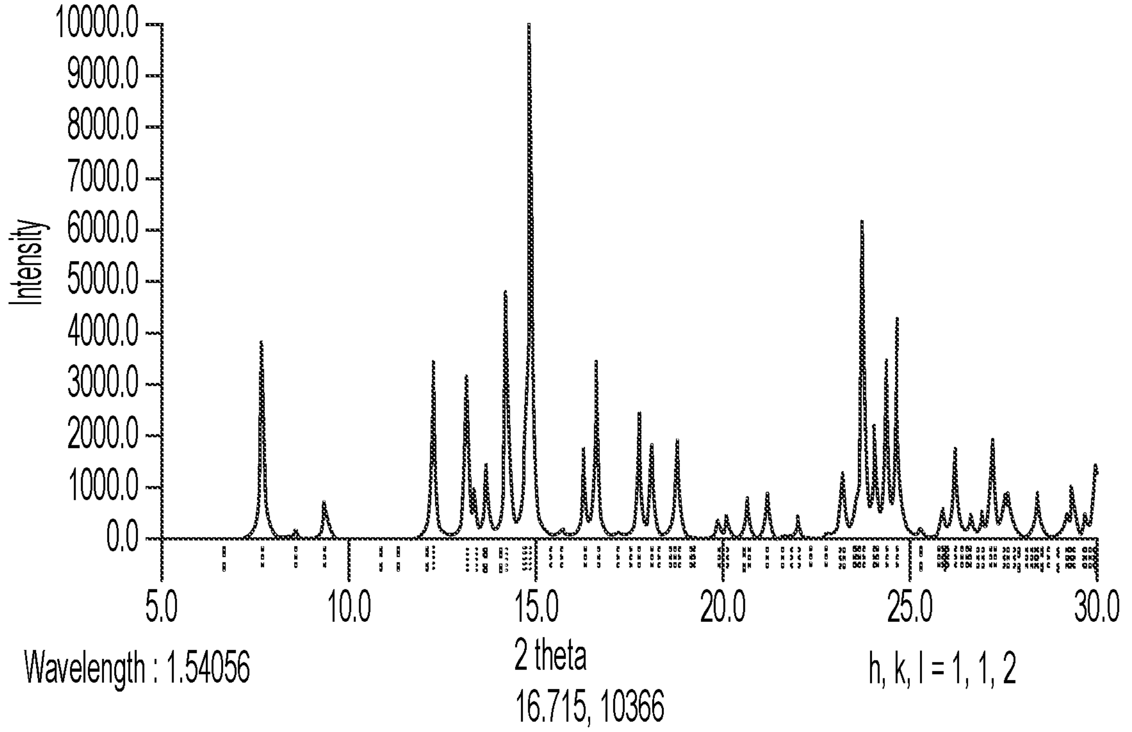
FIG. 13 shows the simulated X-ray powder diffraction pattern (XRPD) for crystalline form 1 of 4-methylcarbonato-N,N-diisopropyltryptramine chloride.

E4. Crystalline form 1 of 4-methylcarbonato-N,N-diisopropyltryptamine chloride according to E3, characterized by at least one of:

- a monoclinic crystal system at a temperature of about 297 K;
- a $P2_{1/n}$ space group at a temperature of about 297 K;
- unit cell dimensions a=13.3128(11) Å, b=7.8017(7) Å, c=18.9739(18) Å, α=90°, β=96.681(3)°, and γ=90°;
- an X-ray powder diffraction pattern substantially similar to FIG. 13; or an X-ray powder diffraction pattern characterized by at least two peaks selected from 7.7, 12.3, and 18.8° 2θ±0.2°2θ.

E5. A composition comprising 4-methylcarbonato-N,N-diisopropyltryptamine chloride according to E1 and an excipient.

E6. A composition comprising crystalline 4-methylcarbonato-N,N-diisopropyltryptamine chloride according to any one of E2-E4 and an excipient.

E7. A composition comprising 4-methylcarbonato-N,N-diisopropyltryptamine chloride according to E1 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E8. A composition comprising crystalline 4-methylcarbonato-N,N-diisopropyltryptamine chloride according to any one of E2-E4 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E9. A method of preventing or treating a psychological disorder comprising the step of:

- administering to a subject in need thereof a therapeutically effective amount of 4-methylcarbonato-N,N-diisopropyltryptamine chloride according to E1.

E10. A method of preventing or treating a psychological disorder comprising the step of:

- administering to a subject in need thereof a therapeutically effective amount of crystalline 4-methylcarbonato-N,N-diisopropyltryptamine chloride according to any one of E2-E4.

E11. A method of preventing or treating a psychological disorder comprising the step of:

- administering to a subject in need thereof a composition according to E5 or E7.

E12. A method of preventing or treating a psychological disorder comprising the step of:

- administering to a subject in need thereof a composition according to E6 or E8.

E13. A method of preventing or treating inflammation and/or pain comprising the step of:

- administering to a subject in need thereof a therapeutically effective amount of 4-methylcarbonato-N,N-diisopropyltryptamine chloride according to E1.

E14. A method of preventing or treating inflammation and/or pain comprising the step of:

- administering to a subject in need thereof a therapeutically effective amount of crystalline 4-methylcarbonato-N,N-diisopropyltryptamine chloride according to any one of E2-E4.

E15. A method of preventing or treating inflammation and/or pain comprising the step of:

- administering to a subject in need thereof a composition according to E5 or E7.

E16. A method of preventing or treating inflammation and/or pain comprising the step of:

- administering to a subject in need thereof a composition according to E6 or E8.

E17. Crystalline [2-(1H-indol-3-yl)ethyl](propan-2-yl) amine (N-isopropyltryptamine).

E18. Crystalline form 1 of [2-(1H-indol-3-yl)ethyl](propan-2-yl)amine (N-isopropyltryptamine).

Figure 14:
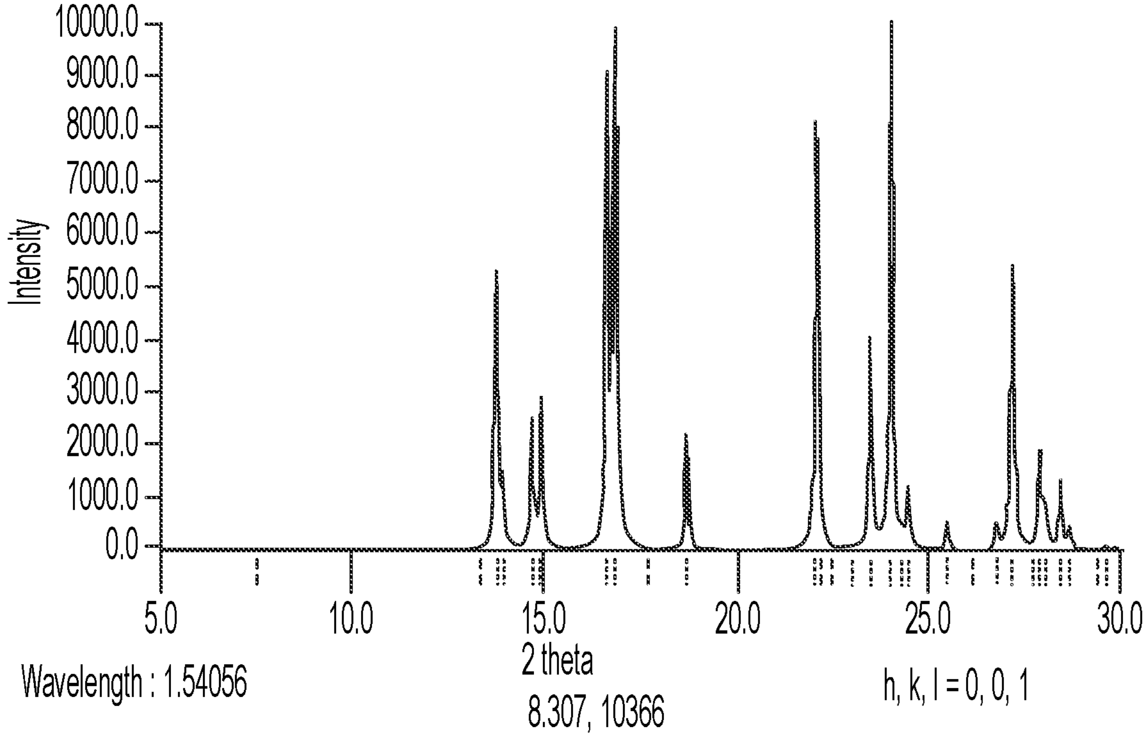
FIG. 14 shows the simulated X-ray powder diffraction pattern (XRPD) for crystalline form 1 of N-isopropyltryptamine.

E19. Crystalline form 1 of N-isopropyltryptamine according to E18, characterized by at least one of:

a monoclinic crystal system at a temperature of about 297 K;

a Cc space group at a temperature of about 297 K;

unit cell dimensions a=13.6490(12) Å, b=7.3196(6) Å, c=12.5727(10) Å, α=90°, β=109.285(3)°, and γ=90°;

an X-ray powder diffraction pattern substantially similar to FIG. 14; or an X-ray powder diffraction pattern characterized by at least two peaks selected from 13.7, 18.7, and 22.1°2θ±0.2°2θ.

E20. A composition comprising crystalline N-isopropyltryptamine according to any one of E17-E19 and an excipient.

E21. A composition comprising crystalline N-isopropyltryptamine according to any one of E17-E19 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E22. A method of preventing or treating a psychological disorder comprising the step of:

administering to a subject in need thereof a therapeutically effective amount of crystalline N-isopropyltryptamine according to any one of E17-E19.

E23. A method of preventing or treating a psychological disorder comprising the step of:

administering to a subject in need thereof a composition according to E20 or E21.

E24. A method of preventing or treating inflammation and/or pain comprising the step of:

administering to a subject in need thereof a therapeutically effective amount of crystalline N-isopropyltryptamine according to any one of E17-E19.

E25. A method of preventing or treating inflammation and/or pain comprising the step of:

administering to a subject in need thereof a composition according to E20 or E21.

E26. Crystalline N-[2-(1H-indol-3-yl)ethyl]propan-2-amine hydrobromide (N-isopropyltryptamine hydrobromide).

E27. Crystalline form 1 of N-[2-(1H-indol-3-yl)ethyl] propan-2-amine hydrobromide (N-isopropyltryptamine hydrobromide).

Figure 15:
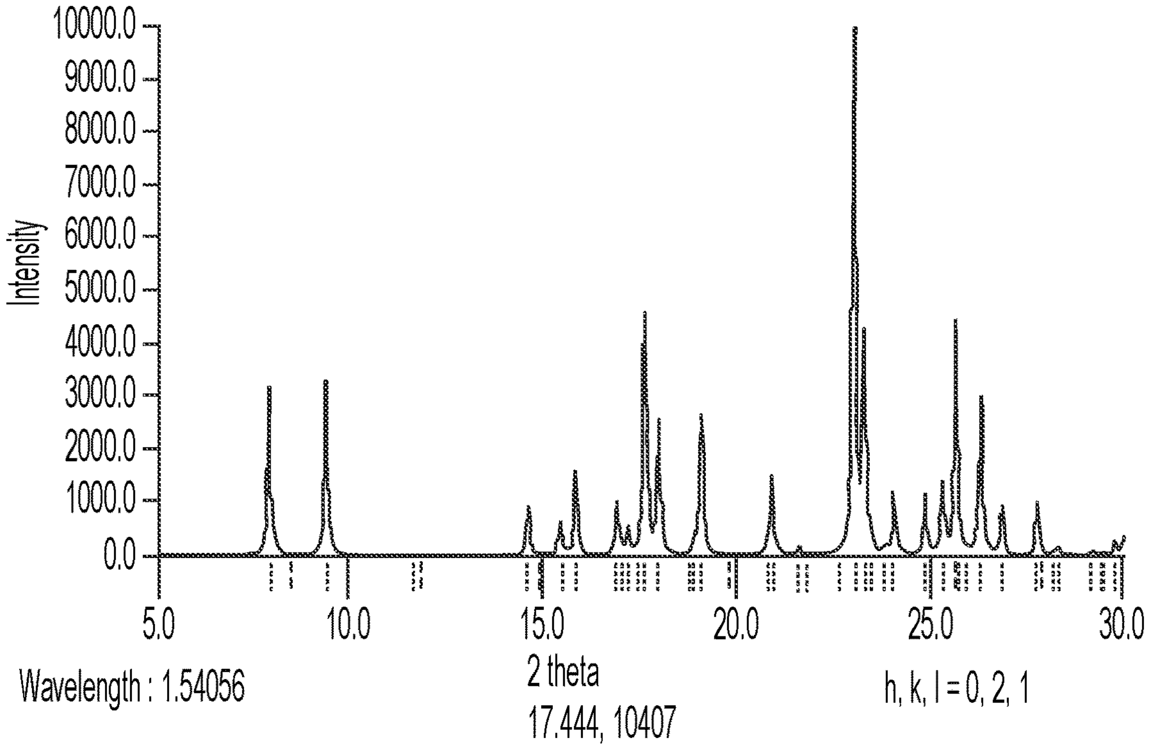
FIG. 15 shows the simulated X-ray powder diffraction pattern (XRPD) for crystalline form 1 of N-isopropyltryptamine hydrobromide.

E28. Crystalline form 1 of N-isopropyltryptamine hydrobromide according to E27, characterized by at least one of:

an orthorhombic crystal system at a temperature of about 297 K;

a $P2_1221$ space group at a temperature of about 297 K;

unit cell dimensions a=5.9418(3) Å, b=10.4163(6) Å, c=22.3928(14) Å, α=90°, β=90°, and γ=90°;

an X-ray powder diffraction pattern substantially similar to FIG. 15; or an X-ray powder diffraction pattern characterized by at least two peaks selected from 7.9, 9.4, and 19.1 °2θ±0.2 °2θ.

E29. A composition comprising crystalline N-isopropyltryptamine hydrobromide according to any one of E26-E28 and an excipient.

E30. A composition comprising crystalline N-isopropyltryptamine hydrobromide according to any one of E26-E28 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E31. A method of preventing or treating a psychological disorder comprising the step of:

administering to a subject in need thereof a therapeutically effective amount of crystalline N-isopropyltryptamine hydrobromide according to any one of E26-E28.

E32. A method of preventing or treating a psychological disorder comprising the step of:

administering to a subject in need thereof a composition according to E29 or E30.

E33. A method of preventing or treating inflammation and/or pain comprising the step of:

administering to a subject in need thereof a therapeutically effective amount of crystalline N-isopropyltryptamine hydrobromide according to any one of E26-E28.

E34. A method of preventing or treating inflammation and/or pain comprising the step of:

administering to a subject in need thereof a composition according to E29 or E30.

E35. Crystalline N-[2-(1H-indol-3-yl)ethyl]cyclohexanamine (N-cyclohexyltryptamine).

E36. Crystalline form 1 of N-[2-(1H-indol-3-yl)ethyl] cyclohexanamine (N-cyclohexyltryptamine).

Figure 16:
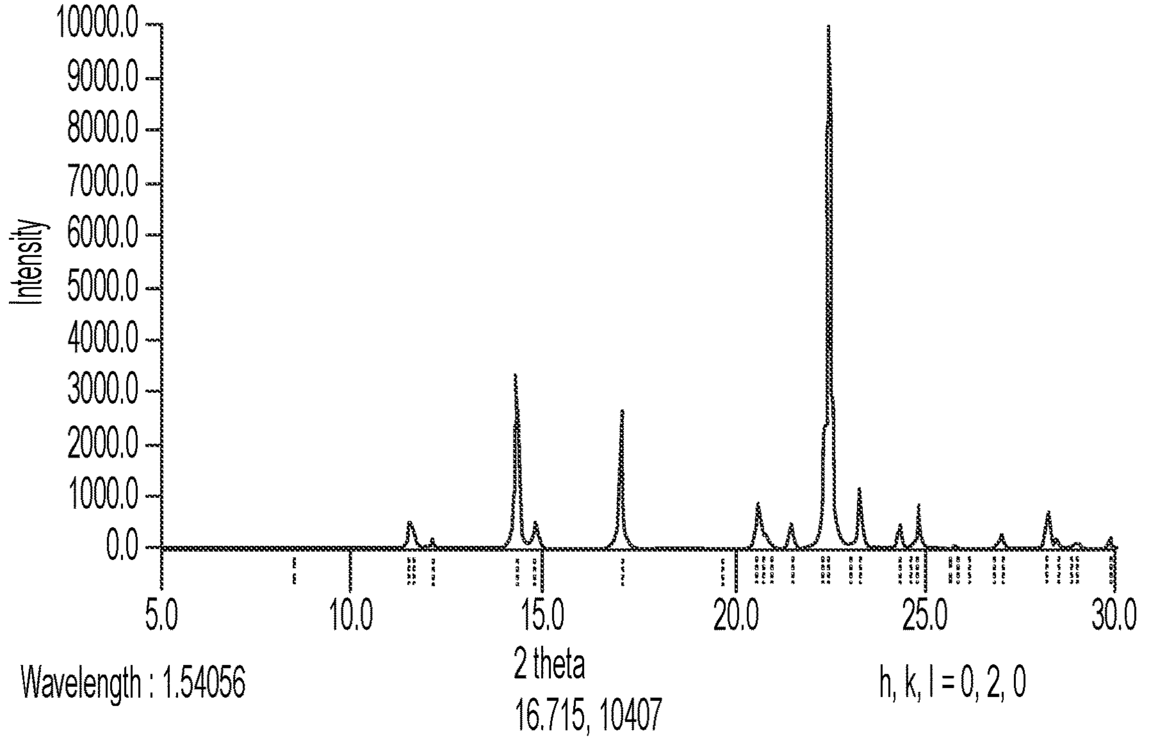
FIG. 16 shows the simulated X-ray powder diffraction pattern (XRPD) for crystalline form 1 of N-cyclohexyltryptamine.

E37. Crystalline form 1 of N-cyclohexyltryptamine according to E36, characterized by at least one of:

a monoclinic crystal system at a temperature of about 297 K;

a $P2_1$ space group at a temperature of about 297 K; unit cell dimensions a=8.5446(6) Å, b=10.3990(7) Å, c=8.6149(6) Å, α=90°, β=116.784(2)°, and γ=90°;

an X-ray powder diffraction pattern substantially similar to FIG. 16; or an X-ray powder diffraction pattern characterized by at least two peaks selected from 14.3, 17.0, and 22.5 °2θ±0.2 °2θ.

E38. A composition comprising crystalline N-cyclohexyltryptamine according to any one of E35-E37 and an excipient.

E39. A composition comprising crystalline N-cyclohexyltryptamine according to any one of E35-E37 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E40. A method of preventing or treating a psychological disorder comprising the step of: administering to a subject in need thereof a therapeutically effective amount of crystalline N-cyclohexyltryptamine according to any one of E35-E37.

E41. A method of preventing or treating a psychological disorder comprising the step of: administering to a subject in need thereof a composition according to E38 or E39.

E42. A method of preventing or treating inflammation and/or pain comprising the step of:

administering to a subject in need thereof a therapeutically effective amount of crystalline N-cyclohexyltryptamine according to any one of E35-E37.

E43. A method of preventing or treating inflammation and/or pain comprising the step of:

administering to a subject in need thereof a composition according to E38 or E39.

E44. Crystalline 2-(1H-indol-3-yl)ethanamine (tryptamine).

E45. Crystalline form 1 of 2-(1H-indol-3-yl)ethanamine (tryptamine).

Figure 17:
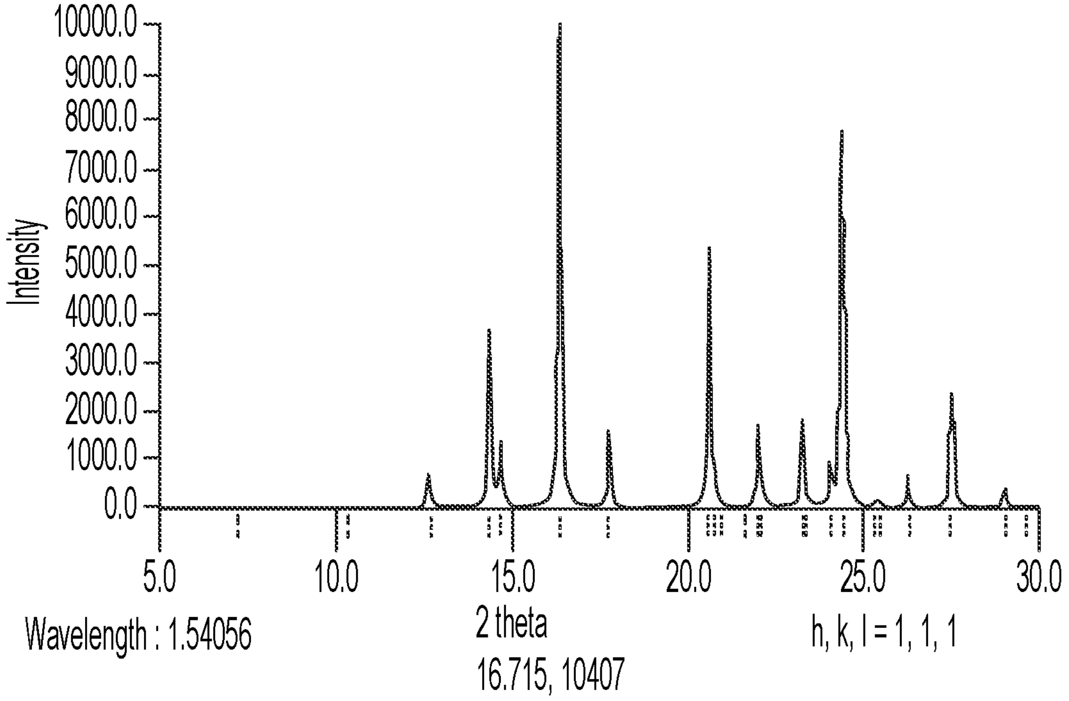
FIG. 17 shows the simulated X-ray powder diffraction pattern (XRPD) for crystalline form 1 of tryptamine.

E46. Crystalline form 1 of tryptamine according to E45, characterized by at least one of: an orthorhombic crystal system at a temperature of about 297 K;

a P2,2,2 space group at a temperature of about 297 K;

unit cell dimensions a=8.4953(6) Å, b=8.5431(7) Å, c=12.2965(8) Å, α=90°, α=90°, and γ=90°;

an X-ray powder diffraction pattern substantially similar to FIG. 17; or an X-ray powder diffraction pattern characterized by at least two peaks selected from 16.4, 17.8, and 20.6 °2θ±0.2 °2θ.

E47. A composition comprising crystalline tryptamine according to any one of E44-E46 and an excipient.

E48. A composition comprising crystalline tryptamine according to any one of E44-E46 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E49. A method of preventing or treating a psychological disorder comprising the step of:

administering to a subject in need thereof a therapeutically effective amount of crystalline tryptamine according to any one of E44-E46.

E50. A method of preventing or treating a psychological disorder comprising the step of:

administering to a subject in need thereof a composition according to E47 or E48.

E51. A method of preventing or treating inflammation and/or pain comprising the step of:

administering to a subject in need thereof a therapeutically effective amount of crystalline tryptamine according to any one of E44-E46.

E52. A method of preventing or treating inflammation and/or pain comprising the step of:

administering to a subject in need thereof a composition according to E47 or E48.

E53. Crystalline N-[2-(1H-indol-3-yl)ethyl]cyclohexanamine hydrobromide (N-cyclohexyltryptamine hydrobromide).

E54. Crystalline form 1 of N-[2-(1H-indol-3-yl)ethyl] cyclohexanamine hydrobromide (N-cyclohexyltryptamine hydrobromide).

Figure 18:
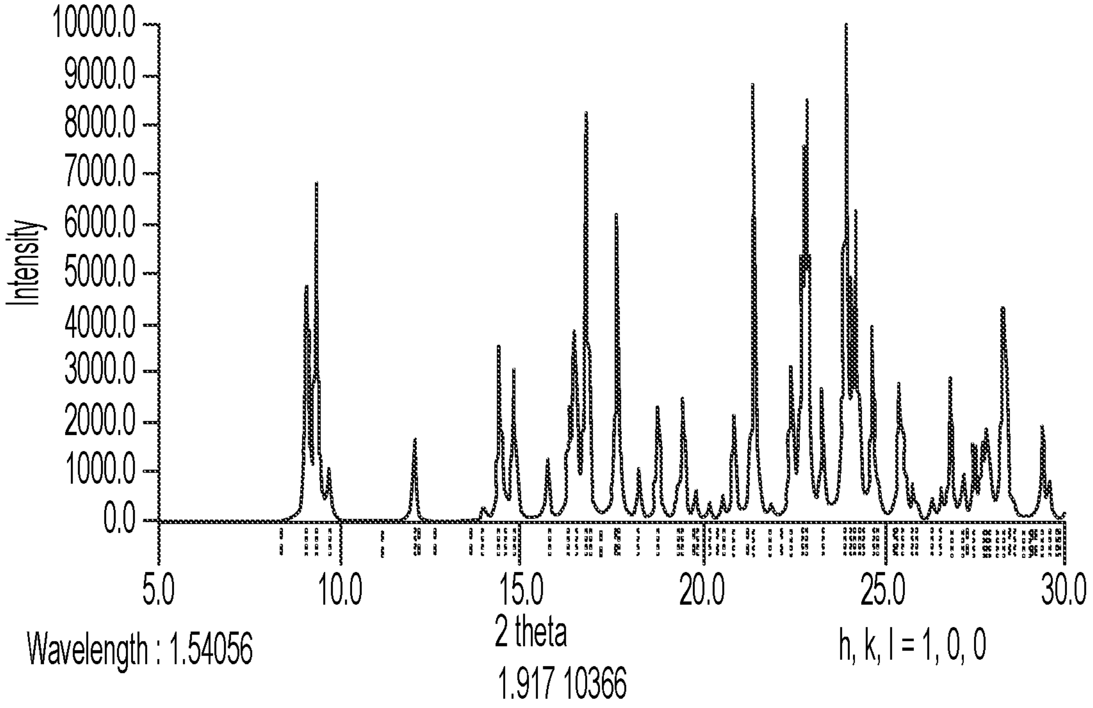
FIG. 18 shows the simulated X-ray powder diffraction pattern (XRPD) for crystalline form 1 of N-cyclohexyltryptamine hydrobromide.

E55. Crystalline form 1 of N-cydohexyltryptamine hydrobromide according to E54, characterized by at least one of:

a monoclinic crystal system at a temperature of about 297 K;

a $P2_1$1~space group at a temperature of about 297 K;

unit cell dimensions a=10.5584(6) Å, b=7.9266(5) Å, c=19.4507(13) Å, α=90°, β=92.406(2)°, and γ=90°;

an X-ray powder diffraction pattern substantially similar to FIG. 18; or an X-ray powder diffraction pattern characterized by at least two peaks selected from 12.0, 17.7, and 18.8 °2θ0.2 °2θ.

E56. A composition comprising crystalline N-cyclohexyltryptamine hydrobromide according to any one of E53-E55 and an excipient.

E57. A composition comprising crystalline N-cyclohexyltryptamine hydrobromide according to any one of E53-E55 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E58. A method of preventing or treating a psychological disorder comprising the step of: administering to a subject in need thereof a therapeutically effective amount of crystalline N-cyclohexyltryptamine hydrobromide according to any one of E53-E55.

E59. A method of preventing or treating a psychological disorder comprising the step of: administering to a subject in need thereof a composition according to E56 or E57.

E60. A method of preventing or treating inflammation and/or pain comprising the step of:

administering to a subject in need thereof a therapeutically effective amount of crystalline N-cyclohexyltryptamine hydrobromide according to any one of E53-E55.

E61. A method of preventing or treating inflammation and/or pain comprising the step of:

administering to a subject in need thereof a composition according to E56 or E57.

Examples

The preparation and characterization of each of crystalline form 1 of (2-{4-[(methoxycarbonyl)oxy]-1H-indol-3-yl}ethyl)bis(propan-2-yl)azanium chloride (4-methylcarbonato-N,N-diisopropyltryptramine chloride or 4-methylcarbonato-DiPT chloride), crystalline form 1 of [2-(1H-indol-3-yl)ethyl](propan-2-yl)amine (N-isopropyltryptamine or NiPT), crystalline form 1 of N-[2-(1H-indol-3-yl)ethyl]propan-2-amine hydrobromide (N-isopropyltryptamine hydrobromide or NiPT hydrobromide), crystalline form 1 of N-[2-(1H-indol-3-yl)ethyl]cyclohexanamine (N-cyclohexyltryptamine), crystalline form 1 of 2-(1H-indol-3-yl)ethanamine (tryptamine), and crystalline form 1 of N-[2-(1H-indol-3-yl)ethyl]cyclohexanamine hydrobromide (N-cyclohexyltryptamine hydrobromide) are described below.

Single Crystal X-Ray Diffraction (SCXRD) Characterization: Data were collected on a Bruker D8 Venture CMOS Diffractometer equipped with an Oxford Cryosystems Cryostream cooling device and using Mo Kα radiation. Structures were solved using the Bruker SHELXTL program and refined with the SHELXTL program as part of the Bruker SHELXTL suite, or OLEX2 software. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Preparation and Characterization of Crystalline Form 1 of 4-Methylcarbonato-DiPT Chloride Synthesis A 3-neck RBF containing a methylene chloride (4 mL) solution 4-hydroxy-N,N-diisopropyltryptamine freebase (90 mg, 1 equiv) was cooled to 0° C. and triethylamine (2 equiv) was added followed by methyl chloroformate (2 equiv) in a dropwise manner. The resulting contents were then stirred at room temperature under an atmosphere of nitrogen for 1.5 hours. The reaction contents were then diluted with methylene chloride (20 mL) and washed three times with distilled water and once with brine. The resulting organic layer was dried using sodium sulphate, filtered and reduced under pressure to afford a residue which was then dissolved in toluene (10 mL). A solution of hydrochloric acid in ether (2M, 1.1 equiv) was added dropwise and stirred at room temperature for 15 minutes. The solvent was removed in vacuo and the residue was suspended in ether and sonicated to afford off-white powder which was filtered and dried under vacuum to yield hydrochloride salt of 4-methylcarbonato-N,N-diisopropyltryptamine (73 mg, 81%).

Crystallization

The powder was recrystallized in methanol to yield single crystals suitable for X-ray analysis.

Single Crystal Characterization

The single crystal data and structure refinement parameters for the crystalline form 1 structure of 4-methylcarbonato-DiPT chloride are reported in Table 3, below.

Preparation and Characterization of Crystalline Form 1 of NiPT

Synthesis

A commercial sample of N-isopropyltryptammonium bromide (ChemBridge) was converted to its freebase by stirring it in a biphasic solution of dichloromethane and aqueous sodium hydroxide. The organic layer was isolated, washed with brined and dried over sodium sulfate. After filtering the sodium sulfate, solvent was removed in vacuo to yield the freebase as a white powder.

Crystallization

Crystals suitable for single crystal X-ray diffraction studies were isolated by the slow evaporation of a dichloromethane solution of the freebase.

Single Crystal Characterization

The single crystal data and structure refinement parameters for the crystalline form 1 structure of NiPT are reported in Table 3, below.

Preparation and Characterization of Crystalline Form 1 of NiPT Hydrobromide

Crystallization

Crystals suitable for single crystal X-ray diffraction studies were grown from the slow evaporation of an ethanol solution of a commercial sample (ChemBridge).

Single Crystal Characterization

The single crystal data and structure refinement parameters for the crystalline form 1 structure of NiPT hydrobromide are reported in Table 3, below.

Preparation and Characterization of Crystalline form 1 of N-cvdohexyltrvptamine

Crystallization

A commercial sample of N-cyclohexyltryptammonium bromide (ChemBridge) was stirred in a biphasic mixture of dichloromethane and aqueous sodium hydroxide. The organic layer was isolated, washed with brine and dried over sodium sulfate. After the sodium sulfate was filtered off, solvent was removed in vacuo to yield the freebase as a white powder. Crystals suitable for single crystal X-ray diffraction studies were grown by the slow evaporation of an acetone solution.

Single Crystal Characterization

The single crystal data and structure refinement parameters for the crystalline form 1 structure of N-cyclohexyltryptamine are reported in Table 3, below.

Preparation and Characterization of Crystalline form 1 of Tryptamine

Crystallization

Single crystals suitable for X-ray diffraction were grown from the slow evaporation of a THF solution of a commercial sample (Alfa Aesar).

Single Crystal Characterization

The single crystal data and structure refinement parameters for the crystalline form 1 structure of tryptamine are reported in Table 3, below.

Preparation and Characterization of Crystalline form 1 of N-cycohexyltryptamine hydrobromide Crystallization Crystals suitable for single crystal X-ray diffraction studies were grown from the slow evaporation of an ethanol solution of a commercial sample (ChemBridge).

Single Crystal Characterization

The single crystal data and structure refinement parameters for the crystalline form 1 structure of N-cyclohexyltryptamine hydrobromide are reported in Table 3, below.

TABLE 3

Single crystal data and structure refinement parameters

| Crystal data | Crystalline form 1 of 4-methylcarbonato-DiPT chloride | Crystalline form 1 of NiPT | Crystalline form 1 of NiPT hydrobromide | Crystalline form 1 of N-cyclohexyl-tryptamine | Crystalline form 1 of Tryptamine | Crystalline form 1 of N-cyclohexyl-tryptamine hydrobromide |
|---|---|---|---|---|---|---|
| Chemical formula | $Cl{\bullet}C_{18}H_{27}N_2O_3$ | $C_{13}H_{18}N_2$ | $Br{\bullet}C_{13}H_{19}N_2$ | $C_{16}H_{22}N_2$ | $C_{10}H_{12}N_2$ | $Br{\bullet}C_{16}H_{23}N_2$ |
| $M_r$ | 354.86 | 202.29 | 283.21 | 242.35 | 160.22 | 323.27 |
| Crystal system, space group | monoclinic, $P2_{1/n}$ | monoclinic, Cc | orthorhombic, $P2_12_12_1$ | monoclinic, $P2_1$ | orthorhombic, $P2_12_12_1$ | monoclinic, $P2_{1/n}$ |
| Temperature (K) | 297(2) | 297(2) | 297(2) | 297(2) | 297(2) | 297(2) |
| a, b, c (Å) | 13.3128(11), 7.8017(7), 18.9739(18) | 13.6490(12), 7.3196(6), 12.5727(10) | 5.9418(3), 10.4163(6), 22.3928(14) | 8.5446(6), 10.3990(7), 8.6149(6) | 8.4953(6), 8.5431(7), 12.2965(8) | 10.5584(6), 7.9266(5), 19.4507(13) |
| α (°) | 90 | 90 | 90 | 90 | 90 | 90 |
| β (°) | 96.681(3) | 109.285(3) | 90 | 116.784(2) | 90 | 92.406(2) |
| γ (°) | 90 | 90 | 90 | 90 | 90 | 90 |
| V ($Å^3$) | 1957.3(3) | 1185.60(17) | 1385.93(14) | 683.35(8) | 892.43(11) | 1626.44(18) |
| Z | 4 | 4 | 4 | 2 | 4 | 4 |
| F(000) | 760 | 440 | 584 | 264 | 344 | 672 |
| $D_x$ (Mg $m^{-3}$) | 1.204 | 1.133 | 1.357 | 1.178 | 1.192 | 1.320 |
| Radiation type | Mo Kα | Mo Kα | Mo Kα | Mo Kα | Mo Kα | Mo Kα |
| λ (Å) | 0.71073 | 0.71073 | 0.71073 | 0.71073 | 0.71073 | 0.71073 |
| θ (°) | 2.83-25.20 | 3.16-26.33 | 3.36-26.20 | 2.65-25.75 | 2.90-26.37 | 2.78-26.29 |

TABLE 3-continued

| Single crystal data and structure refinement parameters | | | | | | |
|---|---|---|---|---|---|---|
| Crystal data | Crystalline form 1 of 4-methylcarbonato-DiPT chloride | Crystalline form 1 of NiPT | Crystalline form 1 of NiPT hydrobromide | Crystalline form 1 of N-cyclohexyl-tryptamine | Crystalline form 1 of Tryptamine | Crystalline form 1 of N-cyclohexyl-tryptamine hydrobromide |
| μ ($mm^{-1}$) | 0.212 | 0.067 | 2.944 | 0.069 | 0.072 | 2.518 |
| Crystal size (mm) | 0.34 × 0.12 × 0.02 | 0.39 × 0.32 × 0.2 | 0.24 × 0.05 × 0.04 | 0.35 × 0.24 × 0.2 | 0.36 × 0.3 × 0.25 | 0.3 × 0.13 × 0.03 |
| Crystal description | block | block | block | block | block | block |
| Crystal color | colourless | colourless | colourless | colourless | colourless | colourless |
| | | | Data collection | | | |
| Diffractometer | Bruker APEX-II CCD | Bruker APEX-II CCD | Bruker APEX-II CCD | Bruker APEX-II CCD | Bruker APEX-II CCD | Bruker APEX-II CCD |
| Absorption correction | Multi-scan SADABS (Bruker, 2016) was used. wR2(int) was 0.0658 before and 0.0578 after correction. The Ratio of minimum to maximum transmission is 0.9136. The λ/2 correction factor is not present. | Multi-scan SADABS (Bruker, 2016) was used. wR2(int) was 0.0551 before and 0.0443 after correction. The Ratio of minimum to maximum transmission is 0.9184. The λ/2 correction factor is not present. | Multi-scan SADABS (Bruker, 2016) was used. wR2(int) was 0.0762 before and 0.0617 after correction. The Ratio of minimum to maximum transmission is 0.8017. The λ/2 correction factor is not present. | Multi-scan SADABS (Bruker, 2016) was used. wR2(int) was 0.0646 before and 0.0539 after correction. The Ratio of minimum to maximum transmission is 0.8650. The λ/2 correction factor is not present. | Multi-scan SADABS (Bruker, 2016) was used. wR2(int) was 0.0593 before and 0.0502 after correction. The Ratio of minimum to maximum transmission is 0.9380. The λ/2 correction factor is not present. | Multi-scan SADABS (Bruker, 2016) was used. wR2(int) was 0.0704 before and 0.0473 after correction. The Ratio of minimum to maximum transmission is 0.8177. The λ/2 correction factor is not present. |
| $T_{min}$, $T_{max}$ | 0.6809, 0.7453 | 0.6846, 0.7454 | 0.5976, 0.7454 | 0.6447, 0.7453 | 0.6992, 0.7454 | 0.6095, 0.7454 |
| No. of measured, independent, and observed [I > 2σ(I)] reflections | 33637, 3730, 2888 | 14315, 2421, 2349 | 24720, 2825, 2445 | 18695, 2621, 2396 | 15588, 1837, 1741 | 46579, 3320, 2978 |
| $R_{int}$ | 0.0531 | 0.0236 | 0.0383 | 0.0341 | 0.0288 | 0.0373 |
| $θ_{max}$, $θ_{min}$ (°) | 25.736, 2.826 | 26.529, 3.201 | 26.421, 2.671 | 25.821, 3.295 | 26.372, 2.903 | 26.404, 3.215 |
| h, k, l | −16 → 16, −9 → 9, −23 → 23 | −16 → 17, −9 → 9, −15 → 15 | −7 → 6, −13 → 13, −28 → 27 | −10 → 10, −12 → 12, −10 → 10 | −10 → 10, −10 → 10, −15 → 15 | −13 → 13, −9 → 9, −24 → 24 |
| | | | Refinement | | | |
| $R[F^2 > 2σ(F^2)]$, $wR(F^2)$, S | 0.0410, 0.1080, 1.037 | 0.0302, 0.0814, 1.053 | 0.0262, 0.0621, 1.013 | 0.0476, 0.1237, 1.040 | 0.0292, 0.0729, 1.087 | 0.0445, 0.1087, 1.224 |
| No. of reflections | 3730 | 2421 | 2825 | 2621 | 1837 | 3320 |
| No. of parameters | 230 | 146 | 160 | 171 | 121 | 184 |
| No. of restraints | 2 | 4 | 3 | 3 | 3 | 3 |
| Absolute structure | — | Flack x determined using 1129 quotients [(I+) − (I−)]/[(I+) + (I−)] (Parsons, Flack and Wagner, Acta Cryst. B69 (2013) 249-259). | Refined as an inversion twin. | Flack x determined using 1039 quotients [(I+) − (I−)]/[(I+) + (I−)] (Parsons, Flack and Wagner, Acta Cryst. B69 (2013) 249-259). | Flack x determined using 701 quotients [(I+) − (I−)]/[(I+) + (I−)] (Parsons, Flack and Wagner, Acta Cryst. B69 (2013) 249-259). | — |
| Absolute structure parameter | — | −0.3(4) | 0.012(15) | 0.5(7) | −0.4(7) | — |
| H-atom treatment | H atoms treated by a mixture of independent and constrained refinement | H atoms treated by a mixture of independent and constrained refinement | H atoms treated by a mixture of independent and constrained refinement | H atoms treated by a mixture of independent and constrained refinement | H atoms treated by a mixture of independent and constrained refinement | H atoms treated by a mixture of independent and constrained refinement |
| w | $w = 1/[σ^2(F_o^2) +$ | $w = 1/[σ^2(F_o^2) +$ | $w = 1/[σ^2(F_o^2) +$ | $w = 1/[σ^2(F_0^2) +$ | $w = 1/[σ^2(F_0^2) +$ | $w = 1/[σ^2(F_0^2) +$ |

TABLE 3-continued

Single crystal data and structure refinement parameters

| Crystal data | Crystalline form 1 of 4-methylcarbonato-DiPT chloride | Crystalline form 1 of NiPT | Crystalline form 1 of NiPT hydrobromide | Crystalline form 1 of N-cyclohexyl-tryptamine | Crystalline form 1 of Tryptamine | Crystalline form 1 of N-cyclohexyl-tryptamine hydrobromide |
|---|---|---|---|---|---|---|
| | $(0.0485P)^2$ + 0.6057P] where P = $(F_o^2 + 2F_C^2)/3$ | $(0.0456P)^2$ + 0.2068P] where P = $(F_o^2 + 2F_c^2)/3$ | $(0.0225P)^2$ + 0.4838P] where P = $(F_o^2 + 2F_C^2)/3$ | $(0.0573P)^2$ + 0.1584P] where P = $(F_0^2 + 2F_C^2)/3$ | $(0.0364P)^2$ + 0.0738P] where P = $(F_o^2 + 2F_C^2)/3$ | 4.8013P] where P = $(F_0^2 + 2F_C^2)/3$ |
| $(\Delta/\sigma)_{max}$ | 0.001 | 0.000 | 0.000 | 0.000 | 0.000 | 0.001 |
| $\Delta\rho_{max}$, $\Delta\rho_{min}$ (e $Å^{-3}$) | 0.217, −0.212 | 0.122, −0.094 | 0.448, −0.414 | 0.259, −0.156 | 0.092, −0.149 | 0.582, −0.702 |
| | Data collection: Bruker APEX4; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009). | Data collection: Bruker APEX4; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009). | Data collection: Bruker APEX4; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009). | Data collection: Bruker APEX4; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009). | Data collection: Bruker APEX4; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009). | Data collection: Bruker APEX4; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009). |

FIG. 1 shows the molecular structure of crystalline form 1 of 4-methyicarbonato-DiPT chloride, showing the atomic labeling.

Figure 2:
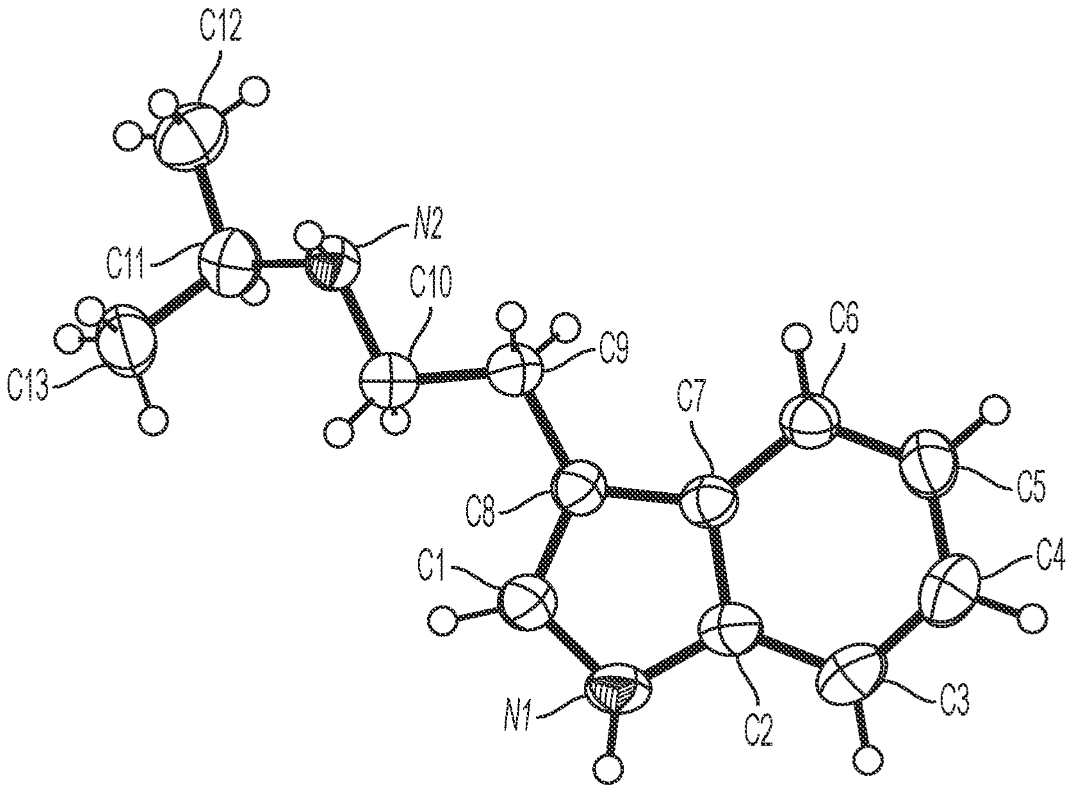
FIG. 2 shows the molecular structure of crystalline form 1 of N-isopropyltryptamine.

FIG. 2 shows the molecular structure of crystalline form 1 of NiPT, showing the atomic labeling.

Figure 3:
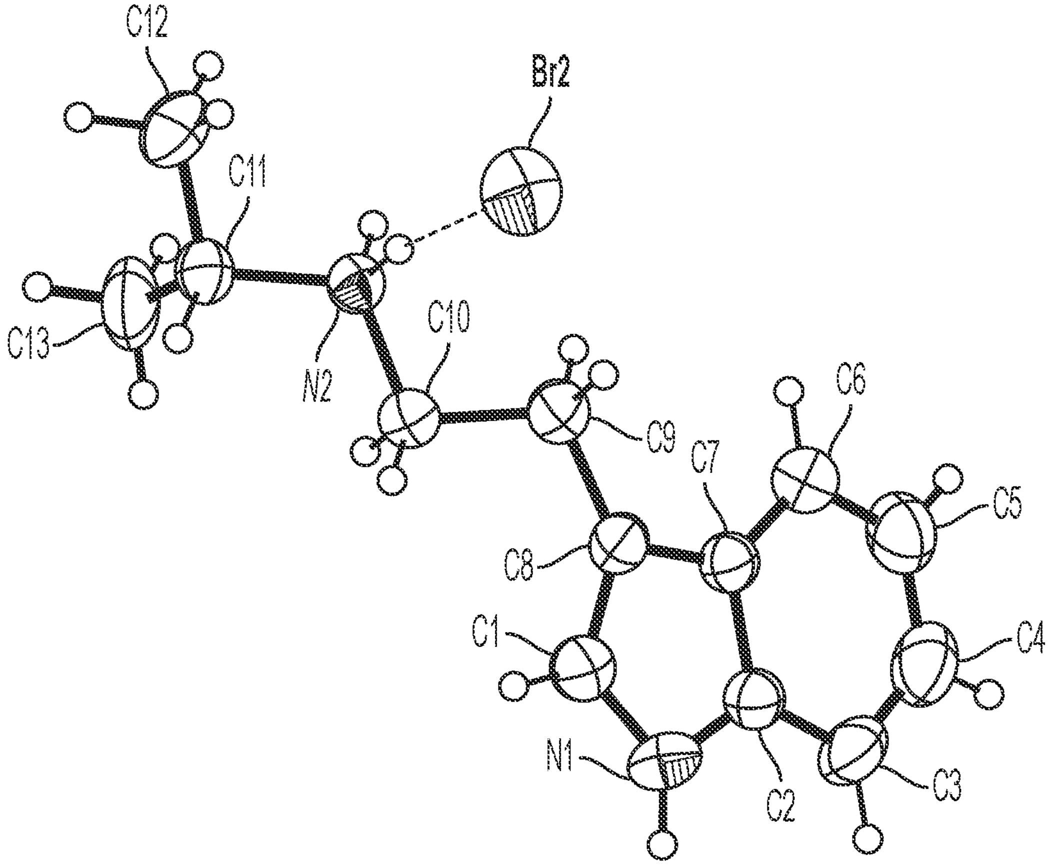
FIG. 3 shows the molecular structure of crystalline form 1 of N-isopropyltryptamine hydrobromide.

FIG. 3 shows the molecular structure of crystalline form 1 of NiPT hydrobromide, showing the atomic labeling.

Figure 4:
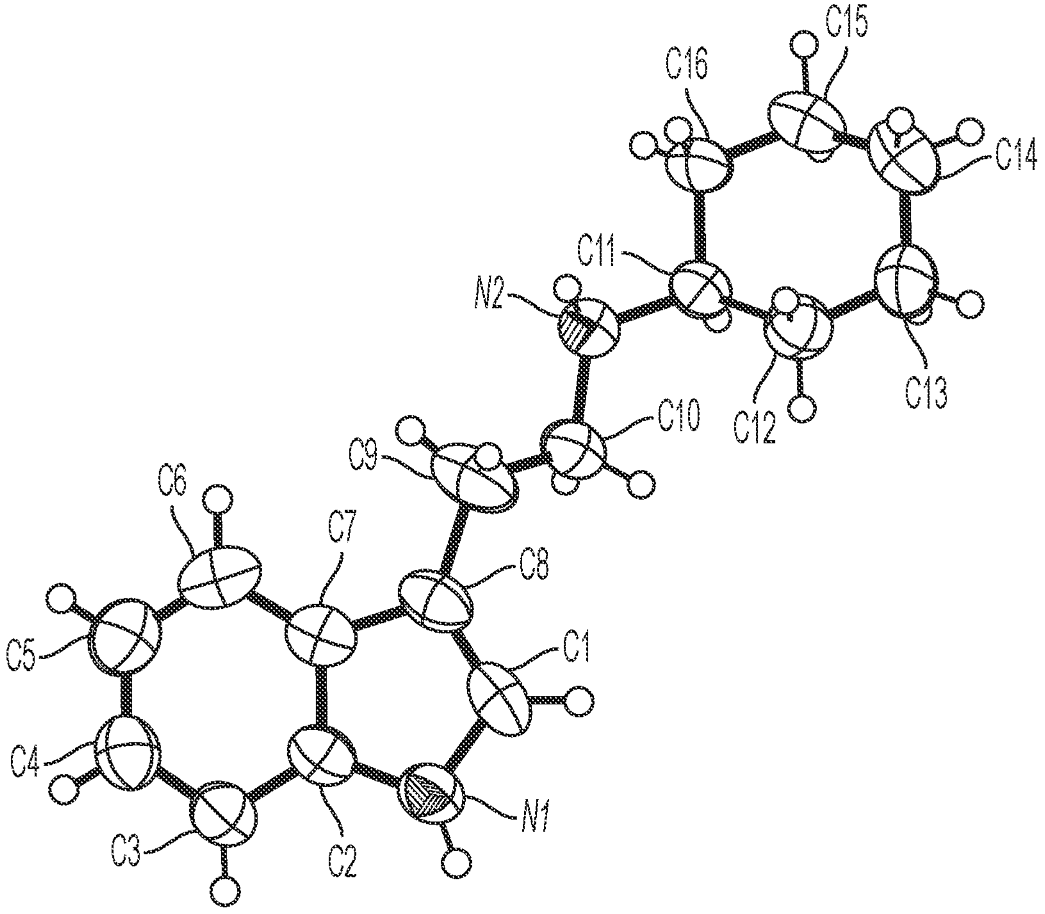
FIG. 4 shows the molecular structure of crystalline form 1 of N-cyclohexyltryptamine.

FIG. 4 shows the molecular structure of crystalline form 1 of N-cyclohexyltryptamine, showing the atomic labeling.

Figure 5:
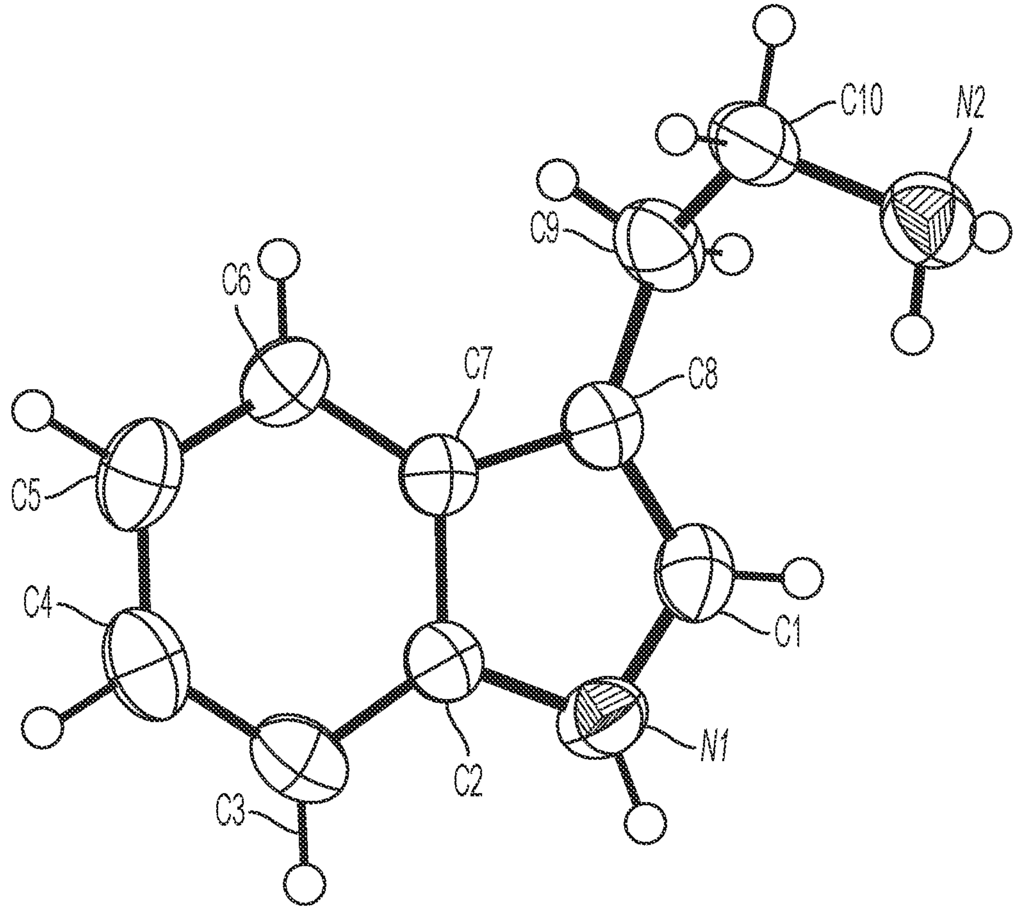
FIG. 5 shows the molecular structure of crystalline form 1 of tryptamine.

FIG. 5 shows the molecular structure of crystalline form 1 of tryptamine, showing the atomic labeling.

Figure 6:
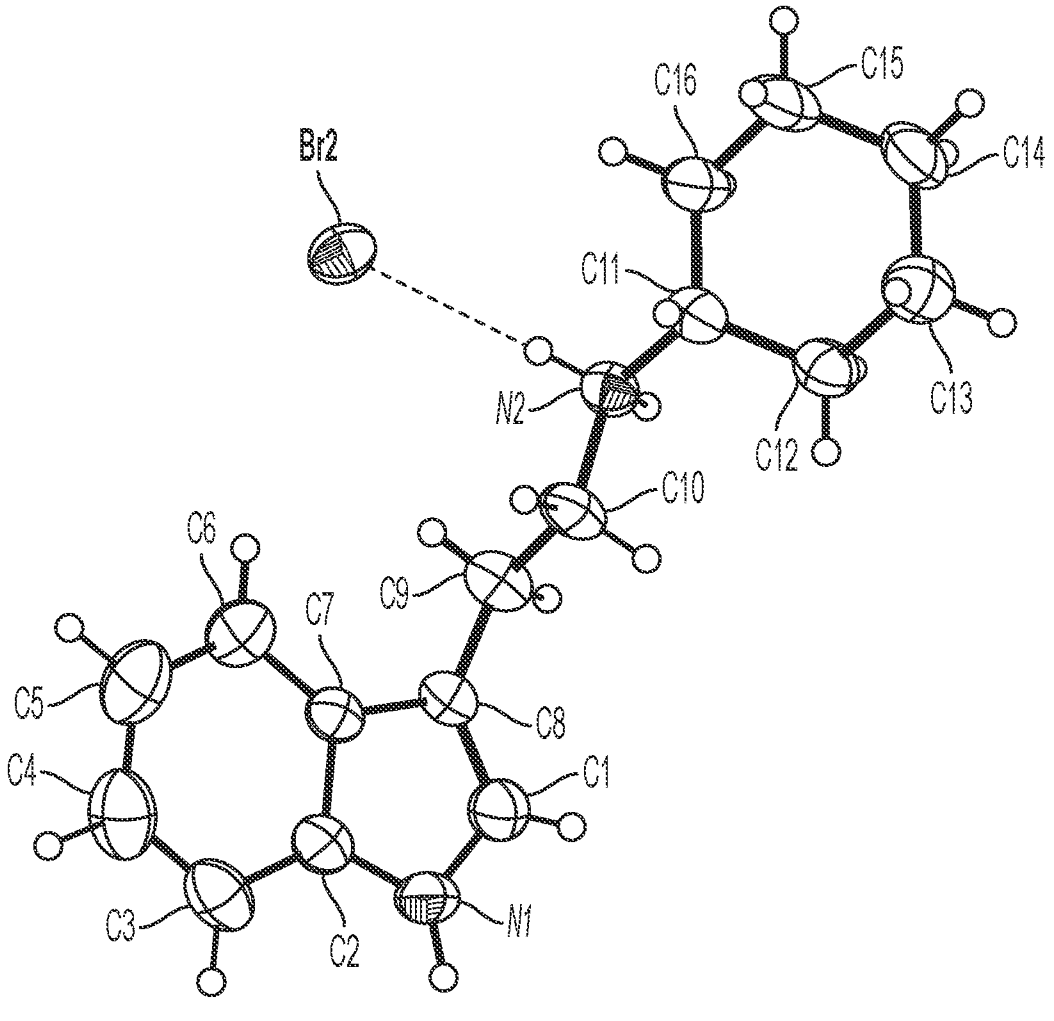
FIG. 6 shows the molecular structure of crystalline form 1 of N-cyclohexyltryptamine hydrobromide.

FIG. 6 shows the molecular structure of crystalline form 1 of N-cyclohexyltryptamine hydrobromide, showing the atomic labeling.

Figure 7:
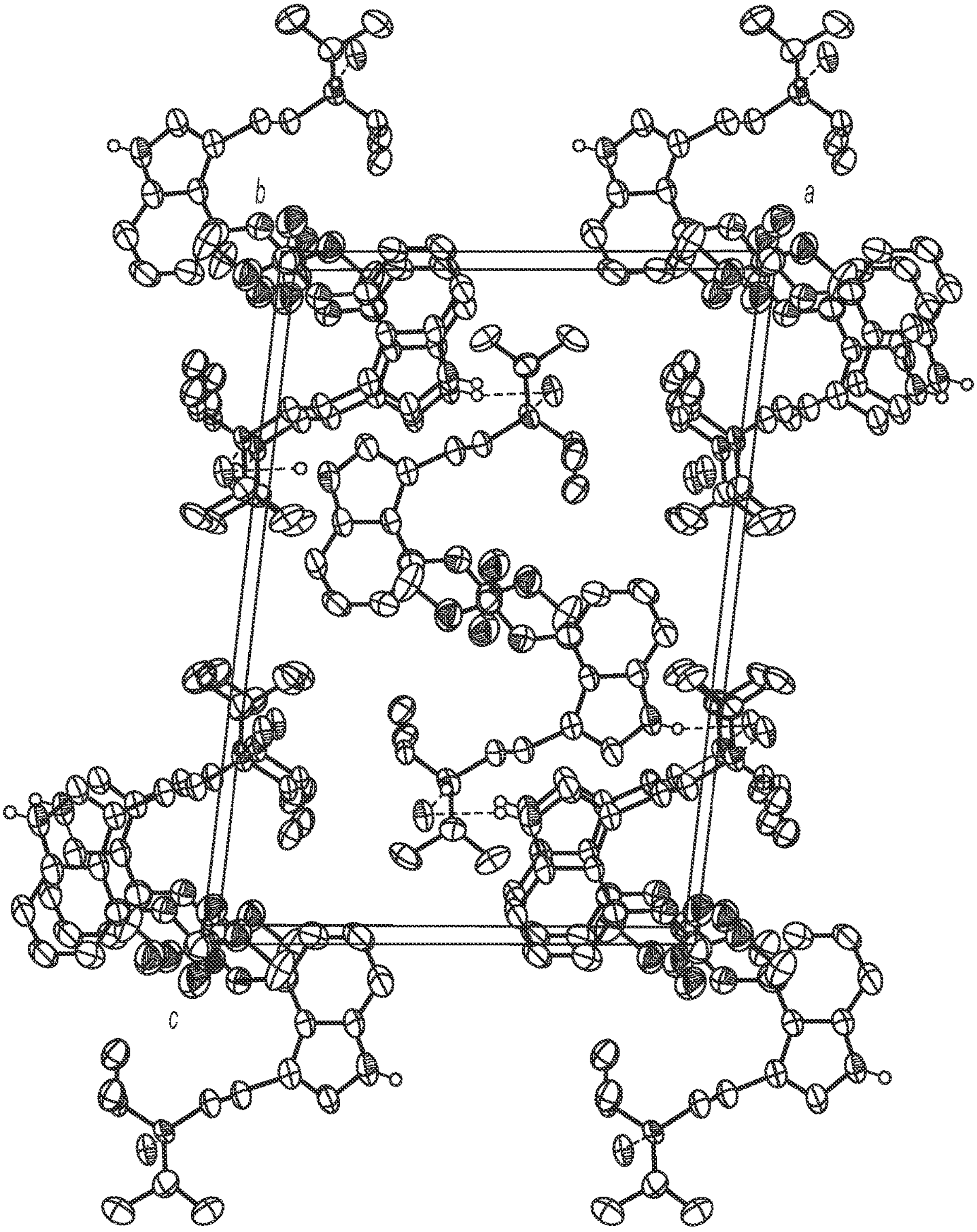
FIG. 7 shows the unit cell of crystalline form 1 of 4-methylcarbonato-N,N-diisopropyltryptramine chloride along the b-axis.

FIG. 7 shows the unit cell of crystalline form 1 of 4-methylcarbonato-DiPT chloride along the b-axis.

Figure 8:
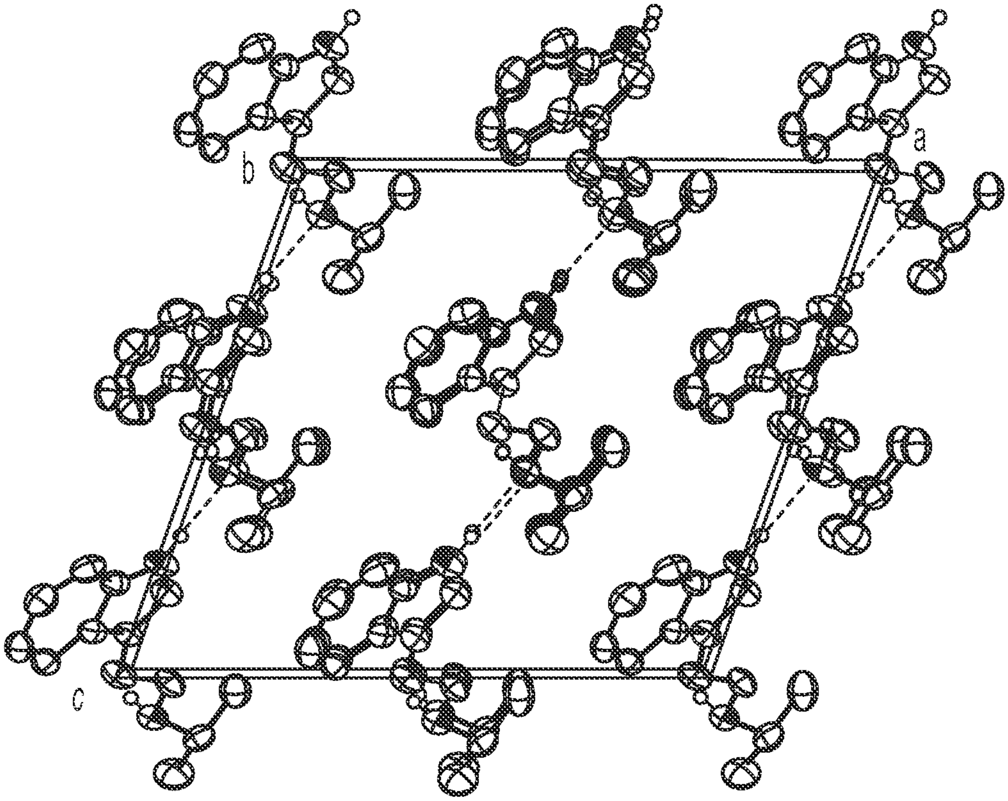
FIG. 8 shows the unit cell of crystalline form 1 of N-isopropyltryptamine along the b-axis.

FIG. 8 shows the unit cell of crystalline form 1 of NiPT along the b-axis.

Figure 9:
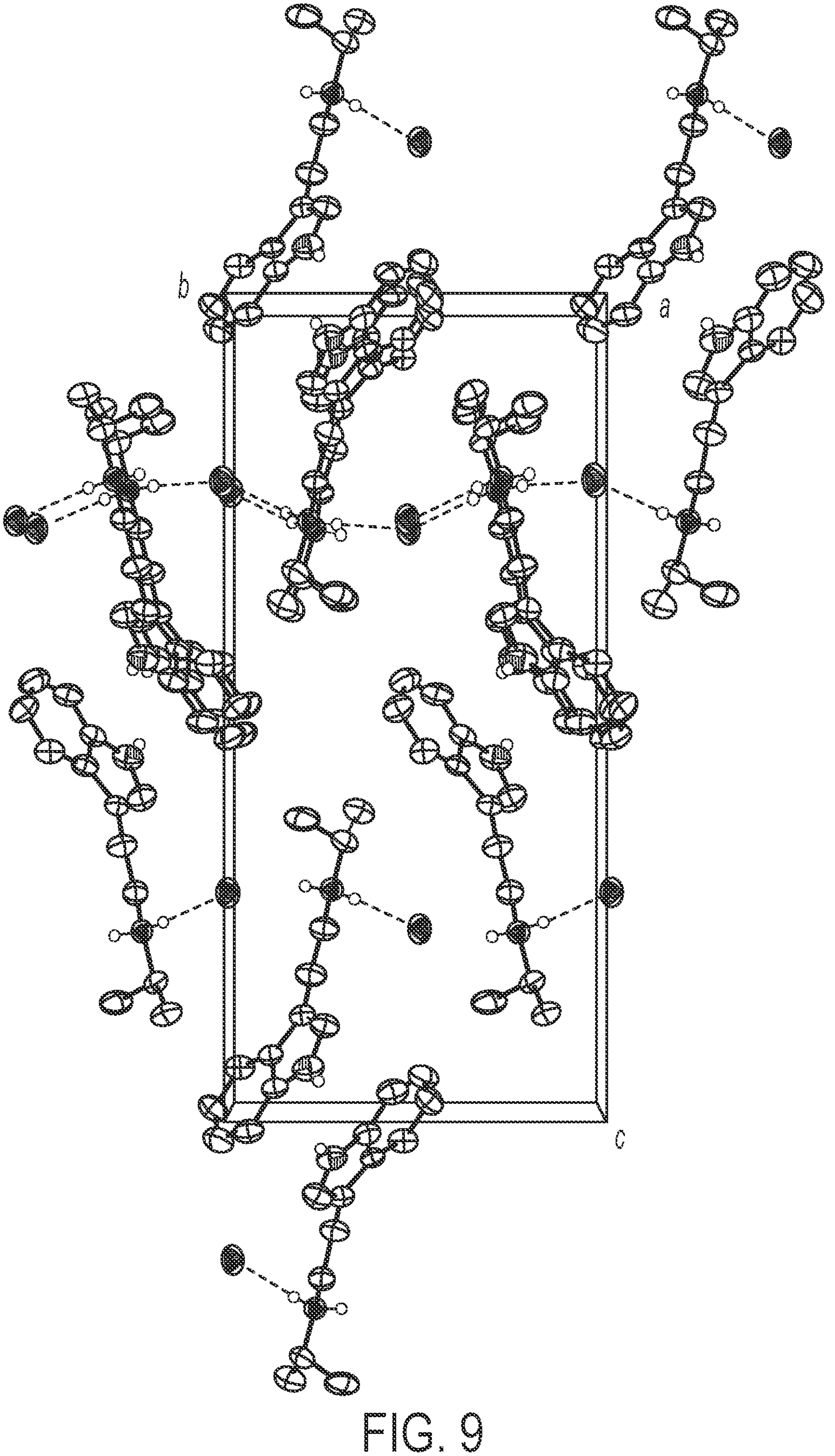
FIG. 9 shows the unit cell of crystalline form 1 of N-isopropyltryptamine hydrobromide along the a-axis.

FIG. 9 shows the unit cell of crystalline form 1 of NiPT hydrobromide along the a-axis.

Figure 10:
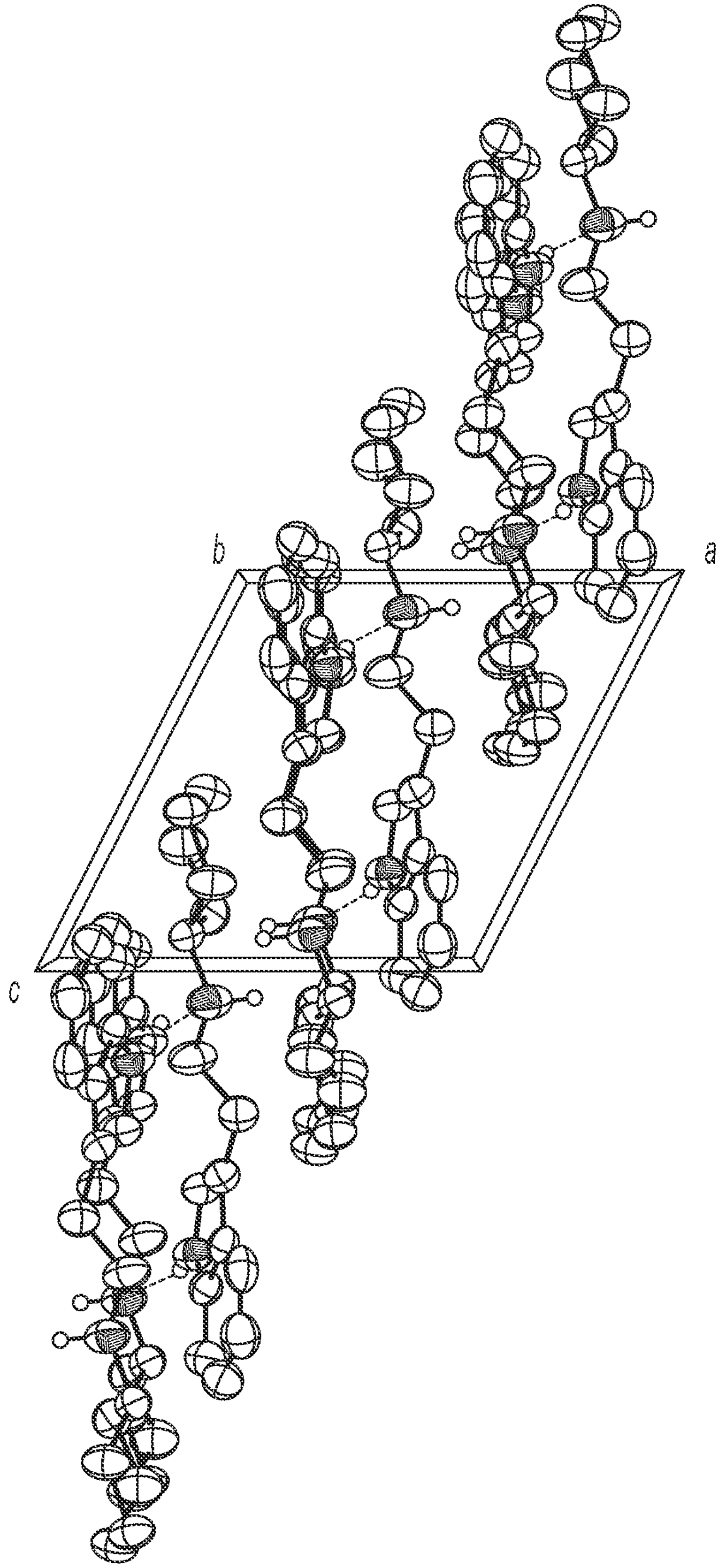
FIG. 10 shows the unit cell of crystalline form 1 of N-cyclohexyltryptamine along the b-axis.

FIG. 10 shows the unit cell of crystalline form 1 of N-cyclohexyltryptamine along the b-axis.

Figure 11:
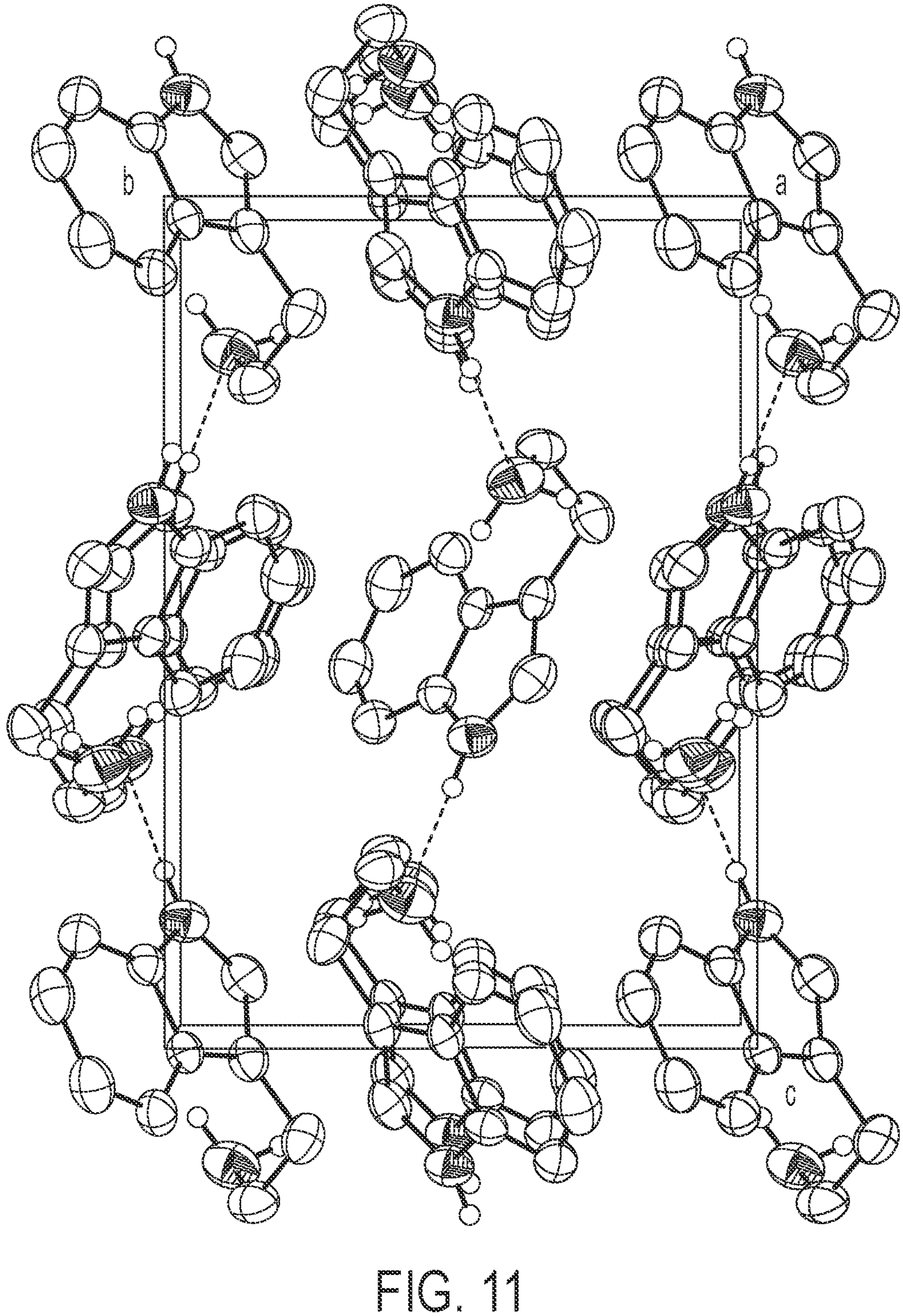
FIG. 11 shows the unit cell of crystalline form 1 of tryptamine along the a-axis.

FIG. 11 shows the unit cell of crystalline form 1 of tryptamine along the a-axis.

Figure 12:
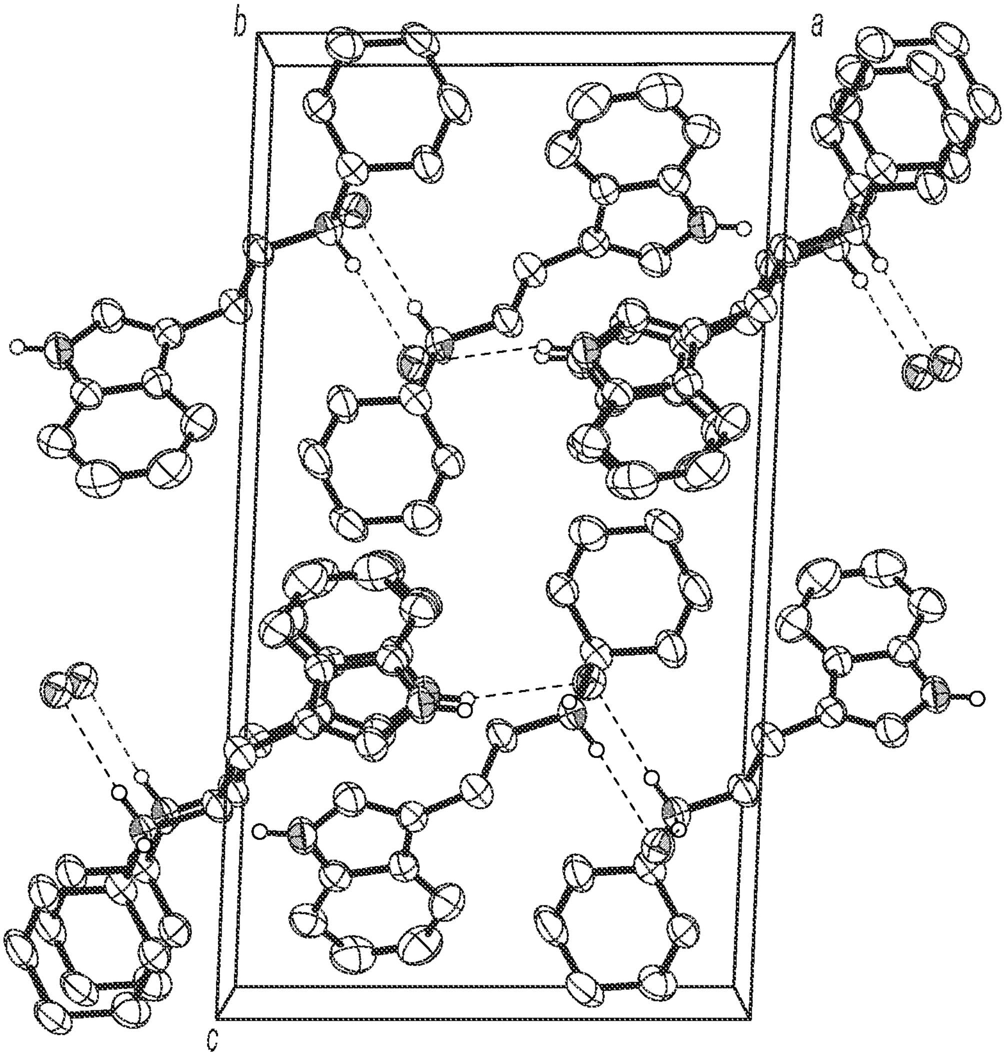
FIG. 12 shows the unit cell of crystalline form 1 of N-cyclohexyltryptamine hydrobromide along the b-axis.

FIG. 12 shows the unit cell of crystalline form 1 of N-cyclohexyltryptamine hydrobromide along the b-axis.

Simulated Powder X-ray Diffraction (PXRD) Pattern

FIG. 13 shows a simulated X-ray powder diffraction pattern (XRPD) for crystalline form 1 of 4-methylcarbonato-DiPT chloride generated from its single crystal data. Table 4 lists the angles, °2θ±0.2° 2θ, and d-spacing of the peaks identified in the experimental XRPD pattern of FIG. 13. The entire list of peaks, or a subset thereof, may be sufficient to characterize the cocrystal. For example, the cocrystal may be characterized by at least two peaks selected from the peaks at 7.7, 12.3, and 18.8 °2θ±0.2° 2θ or their corresponding d-spacing as well as by an XRPD pattern substantially similar to FIG. 13.

Simulated Powder X-ray Diffraction (PXRD) Pattern

FIG. 14 shows a simulated X-ray powder diffraction pattern (XRPD) for crystalline form 1 of NiPT generated from its single crystal data. Table 5 lists the angles, °2θ±0.2°2θ, and d-spacing of the peaks identified in the experimental XRPD pattern of FIG. 14. The entire list of peaks, or a subset thereof, may be sufficient to characterize the cocrystal. For example, the cocrystal may be characterized by at least two peaks selected from the peaks at 13.7, 18.7, and 22.1 °2θ±0.2°2θ or their corresponding d-spacing as well as by an XRPD pattern substantially similar to FIG. 14.

Simulated Powder X-ray Diffraction (PXRD) Pattern

FIG. 15 shows a simulated X-ray powder diffraction pattern (XRPD) for crystalline form 1 of NiPT hydrobromide generated from its single crystal data. Table 6 lists the angles, °2θ±0.2°2θ, and d-spacing of the peaks identified in the experimental XRPD pattern of FIG. 15. The entire list of peaks, or a subset thereof, may be sufficient to characterize the cocrystal. For example, the cocrystal may be characterized by at least two peaks selected from the peaks at 7.9, 9.4, and 19.1 °2θ±0.2° 2θ or their corresponding d-spacing as well as by an XRPD pattern substantially similar to FIG. 15.

Simulated Powder X-ray Diffraction (PXRD) Pattern

FIG. 16 shows a simulated X-ray powder diffraction pattern (XRPD) for crystalline form 1 of N-cyclohexyltryptamine generated from its single crystal data. Table 7 lists the angles, °2θ±0.2°2θ, and d-spacing of the peaks identified in the experimental XRPD pattern of FIG. 16. The entire list of peaks, or a subset thereof, may be sufficient to characterize the cocrystal. For example, the cocrystal may be characterized by at least two peaks selected from the peaks at 14.3, 17.0, and 22.5 °2θ±0.2°2θ or their corresponding d-spacing as well as by an XRPD pattern substantially similar to FIG. 16.

Simulated Powder X-ray Diffraction (PXRD) Pattern

FIG. 17 shows a simulated X-ray powder diffraction pattern (XRPD) for crystalline form 1 of tryptamine generated from its single crystal data. Table 8 lists the angles, °2θ±0.2° 2θ, and d-spacing of the peaks identified in the experimental XRPD pattern of FIG. 17. The entire list of peaks, or a subset thereof, may be sufficient to characterize the cocrystal. For example, the cocrystal may be characterized by at least two peaks selected from the peaks at 16.4, 17.8, and 20.6 °2θ±0.2°2θ or their corresponding d-spacing as well as by an XRPD pattern substantially similar to FIG. 17.

Simulated Powder X-ray Diffraction (PXRD) Pattern

FIG. 18 shows a simulated X-ray powder diffraction pattern (XRPD) for crystalline form 1 of N-cyclohexyltryptamine hydrobromide generated from its single crystal data. Table 9 lists the angles, °2θ±0.2°2θ, and d-spacing of the peaks identified in the experimental XRPD pattern of FIG. 18. The entire list of peaks, or a subset thereof, may be sufficient to characterize the cocrystal. For example, the cocrystal may be characterized by at least two peaks selected from the peaks at 12.0, 17.7, and 18.8 °2θ±0.2°2θ or their corresponding d-spacing as well as by an XRPD pattern substantially similar to FIG. 18.

TABLE 4

| Crystalline form 1 of 4-methylcarbonato-DiPT chloride | | |
|---|---|---|
| d-spacing (Å) | °2θ ± 0.2°2θ | Intensity |
| 11.47 | 7.70 | 7833 |
| 10.28 | 8.60 | 376 |
| 9.42 | 9.38 | 2266 |
| 7.21 | 12.27 | 18548 |
| 6.72 | 13.17 | 19355 |

TABLE 4-continued

| Crystalline form 1 of 4-methylcarbonato-DiPT chloride | | |
|---|---|---|
| d-spacing (Å) | °2θ ± 0.2°2θ | Intensity |
| 6.61 | 13.38 | 4798 |
| 6.45 | 13.72 | 8904 |
| 6.21 | 14.24 | 33887 |
| 6.01 | 14.73 | 11764 |
| 5.95 | 14.88 | 77540 |
| 5.73 | 15.44 | 240 |
| 5.63 | 15.73 | 1215 |
| 5.43 | 16.30 | 15992 |
| 5.32 | 16.64 | 33856 |
| 5.14 | 17.24 | 1203 |
| 5.04 | 17.57 | 56 |
| 4.98 | 17.78 | 26784 |
| 4.89 | 18.12 | 20801 |
| 4.77 | 18.59 | 974 |
| 4.73 | 18.74 | 1729 |
| 4.71 | 18.82 | 23100 |
| 4.62 | 19.19 | 0 |
| 4.46 | 19.89 | 4924 |
| 4.41 | 20.13 | 6162 |
| 4.29 | 20.68 | 12040 |
| 4.19 | 21.21 | 13858 |
| 4.12 | 21.58 | 1203 |
| 4.07 | 21.84 | 572 |
| 4.03 | 22.02 | 7072 |
| 3.97 | 22.38 | 19 |
| 3.90 | 22.78 | 1239 |
| 3.84 | 23.16 | 13552 |
| 3.84 | 23.16 | 350 |
| 3.82 | 23.25 | 20203 |
| 3.82 | 23.27 | 28 |
| 3.77 | 23.56 | 8670 |
| 3.75 | 23.68 | 801 |
| 3.74 | 23.76 | 112810 |
| 3.74 | 23.76 | 13688 |
| 3.69 | 24.08 | 41133 |
| 3.69 | 24.11 | 537 |
| 3.69 | 24.12 | 832 |
| 3.65 | 24.39 | 72259 |
| 3.64 | 24.42 | 399 |
| 3.61 | 24.67 | 4505 |
| 3.60 | 24.68 | 88643 |
| 3.52 | 25.29 | 3 |
| 3.52 | 25.30 | 4218 |
| 3.44 | 25.89 | 7875 |
| 3.43 | 25.92 | 5014 |
| 3.43 | 25.93 | 2363 |
| 3.43 | 25.99 | 1087 |
| 3.39 | 26.24 | 43587 |
| 3.37 | 26.40 | 4001 |
| 3.36 | 26.51 | 1140 |
| 3.34 | 26.65 | 10498 |
| 3.31 | 26.88 | 2 |
| 3.31 | 26.95 | 11100 |
| 3.30 | 27.00 | 1146 |
| 3.27 | 27.21 | 51182 |
| 3.26 | 27.32 | 2921 |
| 3.24 | 27.51 | 18317 |
| 3.23 | 27.63 | 21577 |
| 3.21 | 27.79 | 9291 |
| 3.17 | 28.14 | 113 |
| 3.16 | 28.25 | 256 |
| 3.14 | 28.39 | 5203 |
| 3.14 | 28.43 | 12308 |
| 3.13 | 28.45 | 12586 |
| 3.11 | 28.71 | 1032 |
| 3.06 | 29.19 | 13202 |
| 3.04 | 29.31 | 312 |
| 3.04 | 29.32 | 1138 |
| 3.04 | 29.37 | 30451 |
| 3.01 | 29.64 | 2 |
| 3.00 | 29.71 | 13429 |
| 2.99 | 29.84 | 4241 |
| 2.98 | 29.98 | 46821 |

TABLE 5

| Crystalline form 1 of NiPT | | |
|---|---|---|
| d-spacing (Å) | °2θ ± 0.2°2θ | Intensity |
| 6.44 | 13.74 | 11805 |
| 6.36 | 13.90 | 2488 |
| 6.03 | 14.67 | 6371 |
| 5.93 | 14.92 | 7292 |
| 5.33 | 16.62 | 28779 |
| 5.26 | 16.83 | 33121 |
| 4.74 | 18.69 | 9360 |
| 4.02 | 22.07 | 49354 |
| 3.86 | 23.01 | 244 |
| 3.79 | 23.48 | 26523 |
| 3.70 | 24.01 | 71412 |
| 3.66 | 24.30 | 1173 |
| 3.64 | 24.42 | 264 |
| 3.64 | 24.46 | 7597 |
| 3.50 | 25.45 | 4179 |
| 3.33 | 26.76 | 3850 |
| 3.28 | 27.16 | 50076 |
| 3.22 | 27.67 | 140 |
| 3.21 | 27.79 | 253 |
| 3.20 | 27.89 | 17181 |
| 3.18 | 28.02 | 7568 |
| 3.14 | 28.42 | 13252 |
| 3.11 | 28.63 | 2 |
| 3.11 | 28.65 | 4023 |
| 3.02 | 29.59 | 1468 |

TABLE 6

| Crystalline form 1 of NiPT hydrobromide | | |
|---|---|---|
| d-spacing (Å) | °2θ ± 0.2°2θ | Intensity |
| 11.20 | 7.89 | 8427 |
| 9.44 | 9.36 | 11866 |
| 7.63 | 11.59 | 10 |
| 6.07 | 14.59 | 8000 |
| 5.74 | 15.42 | 5934 |
| 5.60 | 15.82 | 16369 |
| 5.25 | 16.88 | 11147 |
| 5.21 | 17.01 | 1126 |
| 5.16 | 17.17 | 5417 |
| 5.07 | 17.47 | 1948 |
| 5.03 | 17.62 | 59107 |
| 4.93 | 17.97 | 34732 |
| 4.72 | 18.78 | 30 |
| 4.69 | 18.92 | 3153 |
| 4.65 | 19.08 | 39852 |
| 4.27 | 20.78 | 3088 |
| 4.25 | 20.91 | 28652 |
| 4.11 | 21.58 | 3147 |
| 4.07 | 21.79 | 0 |
| 3.92 | 22.68 | 297 |
| 3.86 | 23.03 | 227801 |
| 3.81 | 23.31 | 96403 |
| 3.79 | 23.42 | 500 |
| 3.73 | 23.82 | 3179 |
| 3.70 | 24.05 | 29278 |
| 3.58 | 24.88 | 29915 |
| 3.51 | 25.33 | 36939 |
| 3.47 | 25.67 | 125749 |
| 3.43 | 25.95 | 1406 |
| 3.40 | 26.22 | 9730 |
| 3.38 | 26.33 | 88845 |
| 3.32 | 26.86 | 28896 |
| 3.21 | 27.78 | 32979 |
| 3.16 | 28.21 | 2407 |
| 3.15 | 28.33 | 5779 |
| 3.06 | 29.18 | 3776 |
| 3.03 | 29.42 | 969 |
| 3.02 | 29.51 | 2071 |
| 3.00 | 29.78 | 9570 |

TABLE 7

| Crystalline form 1 of N-cyclohexyltryptamine | | |
|---|---|---|
| d-spacing (Å) | °2θ ± 0.2°2θ | Intensity |
| 7.69 | 11.50 | 640 |
| 7.63 | 11.59 | 580 |
| 7.31 | 12.10 | 283 |
| 6.18 | 14.31 | 7172 |
| 6.15 | 14.39 | 458 |
| 5.98 | 14.81 | 1211 |
| 5.20 | 17.04 | 8239 |
| 4.50 | 19.73 | 29 |
| 4.31 | 20.60 | 1846 |
| 4.30 | 20.64 | 1079 |
| 4.30 | 20.66 | 1766 |
| 4.27 | 20.80 | 1083 |
| 4.24 | 20.95 | 770 |
| 4.13 | 21.51 | 2319 |
| 3.97 | 22.36 | 366 |
| 3.95 | 22.51 | 55830 |
| 3.85 | 23.11 | 15 |
| 3.81 | 23.30 | 6284 |
| 3.65 | 24.34 | 2828 |
| 3.61 | 24.66 | 344 |
| 3.58 | 24.85 | 5490 |
| 3.45 | 25.83 | 685 |
| 3.40 | 26.18 | 34 |
| 3.31 | 26.88 | 452 |
| 3.30 | 27.01 | 2327 |
| 3.16 | 28.22 | 6120 |
| 3.16 | 28.26 | 160 |
| 3.13 | 28.48 | 1517 |
| 3.09 | 28.85 | 892 |
| 3.08 | 29.01 | 1187 |
| 2.99 | 29.87 | 2324 |

TABLE 8

| Crystalline form 1 of tryptamine | | |
|---|---|---|
| d-spacing (Å) | °2θ ± 0.2°2θ | Intensity |
| 7.02 | 12.61 | 411 |
| 6.99 | 12.65 | 926 |
| 6.15 | 14.39 | 7854 |
| 6.02 | 14.69 | 2863 |
| 5.41 | 16.37 | 28525 |
| 4.99 | 17.76 | 35 |
| 4.98 | 17.79 | 5346 |
| 4.30 | 20.62 | 23946 |
| 4.27 | 20.78 | 2212 |
| 4.25 | 20.90 | 146 |
| 4.04 | 22.01 | 8788 |
| 4.01 | 22.12 | 1883 |
| 3.82 | 23.29 | 10630 |
| 3.80 | 23.37 | 608 |
| 3.70 | 24.06 | 2602 |
| 3.69 | 24.09 | 2365 |
| 3.64 | 24.40 | 46241 |
| 3.63 | 24.48 | 13653 |
| 3.51 | 25.37 | 539 |
| 3.49 | 25.47 | 812 |
| 3.39 | 26.28 | 4935 |
| 3.24 | 27.49 | 12628 |
| 3.23 | 27.55 | 15088 |
| 3.07 | 29.02 | 3614 |
| 3.01 | 29.63 | 11 |

TABLE 9

| Crystalline form 1 of N-cyclohexyltryptamine hydrobromide | | |
|---|---|---|
| d-spacing (Å) | °2θ ± 0.2°2θ | Intensity |
| 9.72 | 9.09 | 8717 |
| 9.44 | 9.36 | 13259 |
| 9.11 | 9.70 | 1948 |
| 7.34 | 12.05 | 5582 |
| 6.34 | 13.96 | 976 |
| 6.14 | 14.41 | 17129 |
| 6.07 | 14.58 | 1203 |
| 5.98 | 14.80 | 15138 |
| 5.63 | 15.74 | 7199 |
| 5.42 | 16.34 | 11852 |
| 5.37 | 16.49 | 21884 |
| 5.27 | 16.79 | 52183 |
| 5.25 | 16.88 | 4166 |
| 5.02 | 17.67 | 44941 |
| 4.86 | 18.25 | 7534 |
| 4.72 | 18.79 | 18904 |
| 4.59 | 19.33 | 4301 |
| 4.56 | 19.47 | 21366 |
| 4.47 | 19.83 | 5291 |
| 4.39 | 20.21 | 3484 |
| 4.32 | 20.56 | 4263 |
| 4.25 | 20.88 | 20976 |
| 4.14 | 21.43 | 95034 |
| 4.06 | 21.90 | 2515 |
| 3.96 | 22.41 | 9659 |
| 3.95 | 22.49 | 31675 |
| 3.90 | 22.76 | 51989 |
| 3.88 | 22.88 | 96176 |
| 3.81 | 23.33 | 32108 |
| 3.71 | 23.97 | 128612 |
| 3.70 | 24.05 | 4244 |
| 3.70 | 24.06 | 24682 |
| 3.67 | 24.23 | 79668 |
| 3.65 | 24.34 | 14273 |
| 3.65 | 24.36 | 2011 |
| 3.63 | 24.47 | 602 |
| 3.60 | 24.72 | 54483 |
| 3.58 | 24.87 | 5782 |
| 3.50 | 25.42 | 38110 |
| 3.49 | 25.50 | 2960 |
| 3.49 | 25.53 | 15214 |
| 3.48 | 25.55 | 11742 |
| 3.45 | 25.81 | 10249 |
| 3.44 | 25.92 | 4411 |
| 3.38 | 26.34 | 6947 |
| 3.35 | 26.58 | 9941 |
| 3.32 | 26.86 | 49001 |
| 3.28 | 27.19 | 15055 |
| 3.24 | 27.51 | 964 |
| 3.24 | 27.52 | 24655 |
| 3.21 | 27.73 | 23450 |
| 3.20 | 27.83 | 4474 |
| 3.20 | 27.86 | 23165 |
| 3.19 | 27.94 | 14439 |
| 3.17 | 28.14 | 494 |

TABLE 9-continued

| Crystalline form 1 of N-cyclohexyltryptamine hydrobromide | | |
|---|---|---|
| d-spacing (Å) | °2θ ± 0.2°2θ | Intensity |
| 3.15 | 28.29 | 56783 |
| 3.15 | 28.34 | 32134 |
| 3.14 | 28.40 | 46520 |
| 3.11 | 28.64 | 4975 |
| 3.09 | 28.90 | 962 |
| 3.07 | 29.05 | 1135 |
| 3.04 | 29.38 | 27163 |
| 3.04 | 29.40 | 14574 |
| 3.02 | 29.58 | 14891 |
| 3.00 | 29.77 | 97 |
| 2.99 | 29.86 | 636 |

REFERENCES

Dolomanov, O. V., Bourhis, L J., Gildea, R. J., Howard, J. A. K. & Puschmann, H. (2009). J. Appl. Cryst. 42, 339-341.

Sheldrick, G. M. (2015). Acta Cryst. C71, 3-8.

The invention claimed is:

1. Crystalline form 1 of (2-{4-[(methoxycarbonyl)oxy]-1H-indol-3-yl}ethyl)bis(propan-2-yl)azanium chloride (4-methylcarbonato-N, N-diisopropyltryptramine chloride), characterized by at least one of:

a monoclinic crystal system at a temperature of about 297 K;

a $P2_{1/n}$ space group at a temperature of about 297 K;

unit cell dimensions a=13.3128(11) Å, b=7.8017(7) Å, c=18.9739(18) Å, α=90°, β=96.681(3)°, and γ=90°;

an X-ray powder diffraction pattern substantially similar to FIG. 13; or an X-ray powder diffraction pattern characterized by at least two peaks selected from 7.7, 12.3, and 18.8° 2θ±0.2° 2θ.

2. A composition comprising crystalline (2-{4-[(methoxycarbonyl)oxy]-1H-indol-3-yl}ethyl)bis(propan-2-yl)azanium chloride (4-methylcarbonato-N,N-diisopropyltryptamine chloride) chloride according to claim 1 and an excipient.

3. A composition comprising crystalline (2-{4-[(methoxycarbonyl)oxy]-1H-indol-3-yl}ethyl)bis(propan-2-yl)azanium chloride (4-methylcarbonato-N,N-diisopropyltryptamine chloride) chloride according to claim 1 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

* * * * *